US012773239B2

(12) United States Patent
Jackson et al.

(10) Patent No.: US 12,773,239 B2
(45) Date of Patent: Oct. 27, 2026

(54) BOTTOM-LOADED PIVOTAL BONE ANCHOR WITH SHANK HEAD COLLET CONTAINMENT

(71) Applicant: Roger P. Jackson, Prairie Village, KS (US)

(72) Inventors: Roger P. Jackson, Prairie Village, KS (US); James L. Surber, Kansas City, KS (US)

( * ) Notice: Subject to any disclaimer, the term of this patent is extended or adjusted under 35 U.S.C. 154(b) by 0 days.

(21) Appl. No.: 18/815,731

(22) Filed: Aug. 26, 2024

(65) Prior Publication Data

US 2024/0415550 A1 Dec. 19, 2024

Related U.S. Application Data

(63) Continuation of application No. 17/068,530, filed on Oct. 12, 2020, now Pat. No. 12,108,968, which is a continuation of application No. 16/724,856, filed on Dec. 23, 2019, now Pat. No. 10,806,495, which is a continuation of application No. 16/363,041, filed on Mar. 25, 2019, now Pat. No. 10,512,487, which is a continuation of application No. 15/420,803, filed on Jan. 31, 2017, now Pat. No. 10,238,430, which is a continuation of application No. 14/521,030, filed on Oct. 22, 2014, now Pat. No. 9,566,092.

(60) Provisional application No. 61/896,894, filed on Oct. 29, 2013.

(51) Int. Cl.
*A61B 17/70* (2006.01)

(52) U.S. Cl.
CPC ...... *A61B 17/7037* (2013.01); *A61B 17/7032* (2013.01); *A61B 17/7076* (2013.01)

(58) Field of Classification Search
CPC .................................. A61B 17/7032–17/7037
See application file for complete search history.

(56) References Cited

U.S. PATENT DOCUMENTS

| | | | |
|---|---|---|---|
| 5,669,911 | A | 9/1997 | Errico et al. |
| 5,672,176 | A | 9/1997 | Biedermann et al. |
| 5,690,630 | A | 11/1997 | Errico et al. |
| 5,733,286 | A | 3/1998 | Errico et al. |
| 5,782,833 | A | 7/1998 | Haider |
| 5,797,911 | A | 8/1998 | Sherman et al. |
| 5,885,286 | A | 3/1999 | Sherman et al. |
| 5,891,145 | A | 4/1999 | Morrison et al. |
| 6,010,503 | A | 1/2000 | Richelsoph et al. |
| 6,063,090 | A | 5/2000 | Schläpfer |
| 6,074,391 | A | 6/2000 | Metz-Stavenhagen et al. |
| 6,090,111 | A | 7/2000 | Nichols |

(Continued)

*Primary Examiner* — Julianna N Harvey
(74) *Attorney, Agent, or Firm* — Polsinelli PC

(57) ABSTRACT

A receiver assembly of a pivotal bone anchor includes a receiver housing portion, an expandable collet retainer portion, and an outer sleeve member. The receiver housing portion includes a pair of upright arms defining an open channel configured to receive the elongate rod. The collet retainer portion includes an inner surface defining a center through aperture configured to expandingly receive the head of the shank into the collet retainer portion upon the head being uploaded through a lower collet opening. The outer sleeve member is configured for positioning around the collet retainer portion after uploading the head of the shank of the bone anchor into the collet retainer portion through the lower collet opening.

21 Claims, 14 Drawing Sheets

(56) References Cited

U.S. PATENT DOCUMENTS

| | | | |
|---|---|---|---|
| 6,146,383 | A | 11/2000 | Studer et al. |
| 6,187,005 | B1 | 2/2001 | Brace et al. |
| 6,254,602 | B1 | 7/2001 | Justis |
| 6,280,442 | B1 | 8/2001 | Barker et al. |
| 6,355,040 | B1 | 3/2002 | Richelsoph et al. |
| 6,471,705 | B1 | 10/2002 | Biedermann et al. |
| 6,485,491 | B1 | 11/2002 | Farris et al. |
| 6,485,494 | B1 | 11/2002 | Haider |
| 6,530,929 | B1 | 3/2003 | Justis et al. |
| 6,540,748 | B2 | 4/2003 | Lombardo |
| 6,554,834 | B1 | 4/2003 | Crozet et al. |
| 6,565,565 | B1 | 5/2003 | Yuan et al. |
| 6,626,908 | B2 | 9/2003 | Cooper et al. |
| 6,648,888 | B1 | 11/2003 | Shluzas |
| 6,723,100 | B2 | 4/2004 | Biedermann et al. |
| 6,740,086 | B2 | 5/2004 | Richelsoph |
| 6,835,196 | B2 | 12/2004 | Biedermann et al. |
| 6,837,889 | B2 | 1/2005 | Shluzas |
| 6,905,500 | B2 | 6/2005 | Jeon et al. |
| 6,945,945 | B2 | 9/2005 | Dalton |
| 7,066,937 | B2 | 6/2006 | Shluzas |
| 7,087,057 | B2 | 8/2006 | Konieczynski et al. |
| 7,141,051 | B2 | 11/2006 | Janowski et al. |
| 7,144,396 | B2 | 12/2006 | Shluzas |
| 7,163,539 | B2 | 1/2007 | Abdelgany et al. |
| 7,179,261 | B2 | 2/2007 | Sicvol et al. |
| 7,186,255 | B2 | 3/2007 | Baynham et al. |
| 7,264,621 | B2 | 9/2007 | Coates et al. |
| 7,306,606 | B2 | 12/2007 | Sasing |
| 7,311,712 | B2 | 12/2007 | Dalton |
| 7,377,923 | B2 | 5/2008 | Purcell et al. |
| 7,445,627 | B2 | 11/2008 | Hawkes et al. |
| 7,479,156 | B2 | 1/2009 | Lourdel et al. |
| 7,604,655 | B2 | 10/2009 | Warnick |
| 7,618,444 | B2 | 11/2009 | Shluzas |
| 7,625,396 | B2 | 12/2009 | Jackson |
| 7,662,172 | B2 | 2/2010 | Warnick |
| 7,686,834 | B2 | 3/2010 | Saint Martin |
| 7,686,835 | B2 | 3/2010 | Warnick |
| 7,695,497 | B2 | 4/2010 | Cordaro et al. |
| 7,699,876 | B2 | 4/2010 | Barry et al. |
| 7,717,942 | B2 | 5/2010 | Schumacher |
| 7,722,654 | B2 | 5/2010 | Taylor et al. |
| 7,766,915 | B2 | 8/2010 | Jackson |
| 7,766,945 | B2 | 8/2010 | Nilsson et al. |
| 7,776,067 | B2 | 8/2010 | Jackson |
| 7,789,896 | B2 | 9/2010 | Jackson |
| 7,789,900 | B2 | 9/2010 | Levy et al. |
| 7,811,310 | B2 | 10/2010 | Baker et al. |
| 7,833,250 | B2 | 11/2010 | Jackson |
| 7,833,251 | B1 | 11/2010 | Ahlgren et al. |
| 7,842,073 | B2 | 11/2010 | Richelsoph et al. |
| 7,857,834 | B2 | 12/2010 | Boschert |
| 7,875,065 | B2 | 1/2011 | Jackson |
| 7,896,902 | B2 | 3/2011 | Jeon et al. |
| 7,901,436 | B2 | 3/2011 | Baccelli |
| 7,905,907 | B2 | 3/2011 | Spitler et al. |
| 7,909,830 | B2 | 3/2011 | Frigg et al. |
| 7,914,536 | B2 | 3/2011 | MacDonald et al. |
| 7,922,748 | B2 | 4/2011 | Hoffman |
| 7,935,135 | B2 | 5/2011 | Mujwid |
| 7,942,909 | B2 | 5/2011 | Hammill, Sr. et al. |
| 7,947,065 | B2 | 5/2011 | Hammill, Sr. et al. |
| 7,951,172 | B2 | 5/2011 | Chao et al. |
| 7,951,173 | B2 | 5/2011 | Hammill, Sr. et al. |
| 7,955,359 | B2 | 6/2011 | Matthis et al. |
| 7,967,850 | B2 | 6/2011 | Jackson |
| 7,972,364 | B2 | 7/2011 | Biedermann et al. |
| 7,988,694 | B2 | 8/2011 | Barrus et al. |
| 8,021,397 | B2 | 9/2011 | Farris et al. |
| 8,034,089 | B2 | 10/2011 | Matthis et al. |
| 8,048,112 | B2 | 11/2011 | Suzuki et al. |
| 8,066,744 | B2 | 11/2011 | Justis et al. |
| 8,075,603 | B2 | 12/2011 | Hammill, Sr. et al. |
| 8,083,776 | B2 | 12/2011 | Alvarez |
| 8,097,025 | B2 | 1/2012 | Hawkes et al. |
| 8,133,262 | B2 | 3/2012 | Whipple |
| 8,162,985 | B2 | 4/2012 | Kim |
| 8,197,517 | B1 | 6/2012 | Lab et al. |
| 8,197,518 | B2 | 6/2012 | Hammill, Sr. et al. |
| 8,221,472 | B2 | 7/2012 | Peterson et al. |
| 8,308,782 | B2 | 11/2012 | Jackson |
| 8,328,817 | B2 | 12/2012 | Strauss |
| 8,353,932 | B2 | 1/2013 | Jackson |
| 8,361,123 | B2 | 1/2013 | Fanger et al. |
| 8,361,129 | B2 | 1/2013 | Chao |
| 8,366,753 | B2 | 2/2013 | Jackson |
| 8,382,805 | B2 | 2/2013 | Wang et al. |
| 8,398,683 | B2 | 3/2013 | Berrevoets et al. |
| 8,439,922 | B1 | 5/2013 | Arnold et al. |
| 8,444,681 | B2 | 5/2013 | Jackson et al. |
| 8,449,578 | B2 | 5/2013 | Keiser et al. |
| 8,506,601 | B2 | 8/2013 | Gephart et al. |
| 8,506,609 | B2 | 8/2013 | Biedermann et al. |
| 8,556,938 | B2 | 10/2013 | Jackson et al. |
| 8,562,652 | B2 | 10/2013 | Biedermann et al. |
| 8,628,558 | B2 | 1/2014 | Harvey et al. |
| 8,657,858 | B2 | 2/2014 | Garamszegi et al. |
| 8,663,290 | B2 | 3/2014 | Doubler et al. |
| 8,663,291 | B2 | 3/2014 | Doubler et al. |
| 8,663,298 | B2 | 3/2014 | Keyer et al. |
| 8,696,712 | B2 | 4/2014 | Biedermann et al. |
| 8,876,869 | B1 | 11/2014 | Schafer et al. |
| 8,882,817 | B2 | 11/2014 | Jones et al. |
| 8,888,827 | B2 | 11/2014 | Harper et al. |
| 8,926,671 | B2 | 1/2015 | Biedermann et al. |
| 8,951,290 | B2 | 2/2015 | Hammer et al. |
| 8,986,349 | B1 | 3/2015 | German et al. |
| 8,998,959 | B2 | 4/2015 | Jackson et al. |
| 9,044,272 | B2 | 6/2015 | Shaffrey et al. |
| 9,060,814 | B2 | 6/2015 | Doubler et al. |
| 9,078,705 | B2 | 7/2015 | Matthis et al. |
| 9,119,674 | B2 | 9/2015 | Matthis et al. |
| 9,155,567 | B2 | 10/2015 | Auerbach et al. |
| 9,168,069 | B2 | 10/2015 | Jackson et al. |
| 9,198,695 | B2 | 12/2015 | Shluzas et al. |
| 9,254,150 | B2 | 2/2016 | Biedermann et al. |
| 9,259,247 | B2 | 2/2016 | Chandanson et al. |
| 9,358,047 | B2 | 6/2016 | Mishra et al. |
| 9,439,680 | B2 | 9/2016 | Biedermann et al. |
| 9,445,847 | B2 | 9/2016 | Biedermann et al. |
| 9,453,526 | B2 | 9/2016 | Black et al. |
| 9,480,517 | B2 | 11/2016 | Jackson et al. |
| 9,486,246 | B2 | 11/2016 | Biedermann et al. |
| 9,492,204 | B2 | 11/2016 | Biedermann et al. |
| 9,526,529 | B2 | 12/2016 | Charvet |
| 9,566,092 | B2 | 2/2017 | Jackson et al. |
| 9,572,600 | B2 | 2/2017 | Biedermann et al. |
| 9,603,627 | B2 | 3/2017 | Krüger |
| 9,615,858 | B2 | 4/2017 | Doubler et al. |
| 9,649,134 | B2 | 5/2017 | Hannen |
| 9,655,652 | B2 | 5/2017 | Biedermann et al. |
| 9,707,013 | B2 | 7/2017 | Rezach et al. |
| 9,724,145 | B2 | 8/2017 | Spratt et al. |
| 9,763,702 | B2 | 9/2017 | Schlaepfer et al. |
| 9,775,660 | B2 | 10/2017 | Spratt et al. |
| 9,782,204 | B2 | 10/2017 | Spratt et al. |
| 9,907,574 | B2 | 3/2018 | Jackson et al. |
| 9,918,745 | B2 | 3/2018 | Jackson et al. |
| 9,924,971 | B2 | 3/2018 | Biedermann et al. |
| 9,924,975 | B2 | 3/2018 | Jackson et al. |
| 9,980,753 | B2 | 5/2018 | Jackson et al. |
| 10,028,770 | B2 | 7/2018 | Rezach et al. |
| 10,039,572 | B2 | 8/2018 | Harris et al. |
| 10,052,136 | B2 | 8/2018 | Nelson |
| 10,058,354 | B2 | 8/2018 | Jackson et al. |
| 10,064,657 | B2 | 9/2018 | Spitler |
| 10,064,658 | B2 | 9/2018 | Jackson et al. |
| 10,117,680 | B2 | 11/2018 | Trautwein et al. |
| 10,154,859 | B2 | 12/2018 | Keyer et al. |
| 10,172,647 | B2 | 1/2019 | Elsbury |
| 10,188,432 | B2 | 1/2019 | Jackson et al. |
| 10,285,738 | B1 | 5/2019 | Doubler et al. |
| 10,335,203 | B2 | 7/2019 | Fiechter et al. |

(56) References Cited

U.S. PATENT DOCUMENTS

| | | | |
|---|---|---|---|
| 10,335,204 B2 | 7/2019 | Matthis et al. | |
| 10,363,070 B2 | 7/2019 | Jackson et al. | |
| 10,463,402 B2 | 11/2019 | Biester et al. | |
| 10,485,594 B2 | 11/2019 | Toon et al. | |
| 10,492,833 B2 | 12/2019 | Biedermann | |
| 10,507,043 B1 | 12/2019 | Gladieux | |
| 10,517,645 B2 | 12/2019 | van der Pol | |
| 10,695,100 B2 | 6/2020 | May et al. | |
| 10,751,090 B2 | 8/2020 | Biedermann et al. | |
| 10,792,074 B2 | 10/2020 | Jackson | |
| 10,898,233 B2 | 1/2021 | Jackson et al. | |
| 10,966,760 B2 | 4/2021 | Armstrong et al. | |
| 11,109,895 B2 | 9/2021 | May et al. | |
| 11,234,738 B2 | 2/2022 | Jackson et al. | |
| 11,234,745 B2 | 2/2022 | Jackson | |
| 2003/0149431 A1 | 8/2003 | Varieur | |
| 2004/0102781 A1 | 5/2004 | Jeon | |
| 2004/0186473 A1 | 9/2004 | Cournoyer et al. | |
| 2004/0260283 A1 | 12/2004 | Wu et al. | |
| 2005/0080415 A1 | 4/2005 | Keyer et al. | |
| 2005/0203516 A1 | 9/2005 | Biedermann et al. | |
| 2006/0025767 A1 | 2/2006 | Khalili | |
| 2006/0058788 A1 | 3/2006 | Hammer et al. | |
| 2006/0161152 A1 | 7/2006 | Ensign et al. | |
| 2006/0161153 A1 | 7/2006 | Hawkes et al. | |
| 2006/0217716 A1 | 9/2006 | Baker et al. | |
| 2007/0118123 A1 | 5/2007 | Strausbaugh et al. | |
| 2007/0270807 A1 | 11/2007 | Armstrong et al. | |
| 2007/0270813 A1 | 11/2007 | Garamszegi | |
| 2008/0004625 A1 | 1/2008 | Runco et al. | |
| 2008/0015576 A1 | 1/2008 | Whipple | |
| 2008/0108992 A1* | 5/2008 | Barry ................. | A61B 17/7037 606/103 |
| 2009/0204155 A1 | 8/2009 | Aschmann | |
| 2010/0010540 A1 | 1/2010 | Park | |
| 2010/0152787 A1 | 6/2010 | Walsh et al. | |
| 2010/0331887 A1 | 12/2010 | Jackson et al. | |
| 2011/0040335 A1 | 2/2011 | Stihl et al. | |
| 2011/0040338 A1 | 2/2011 | Jackson | |
| 2011/0270321 A1 | 11/2011 | Prevost et al. | |
| 2012/0095516 A1* | 4/2012 | Dikeman ........... | A61B 17/7037 606/305 |
| 2012/0310284 A1 | 12/2012 | Gerchow | |
| 2013/0085536 A1* | 4/2013 | Biedermann ...... | A61B 17/7035 606/328 |
| 2013/0096623 A1* | 4/2013 | Biedermann ...... | A61B 17/7037 606/279 |
| 2013/0103098 A1 | 4/2013 | Jackson et al. | |
| 2013/0144346 A1 | 6/2013 | Jackson et al. | |
| 2013/0150852 A1* | 6/2013 | Shluzas .............. | A61B 17/7032 606/65 |
| 2013/0218213 A1 | 8/2013 | Lemoine | |
| 2014/0025119 A1 | 1/2014 | Biedermann et al. | |
| 2014/0121703 A1 | 5/2014 | Jackson et al. | |
| 2018/0243010 A1 | 8/2018 | Murabayashi et al. | |

* cited by examiner

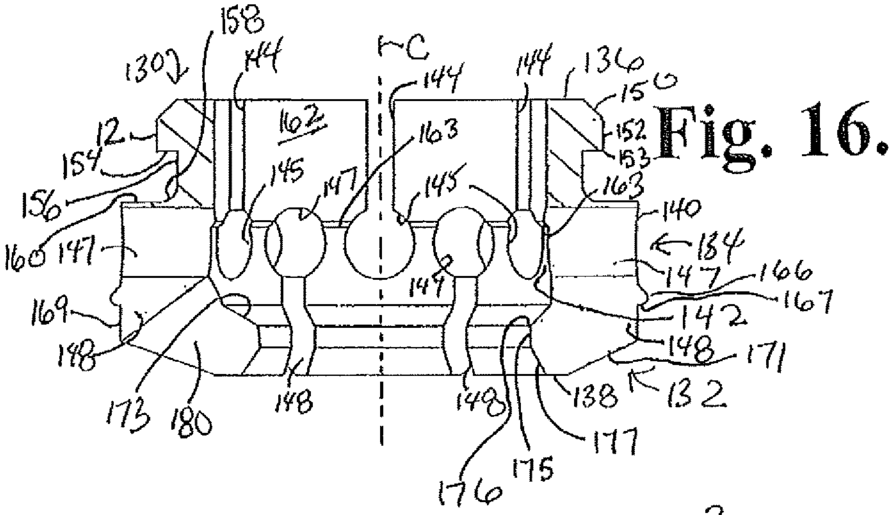
Fig. 16.
Fig. 17.
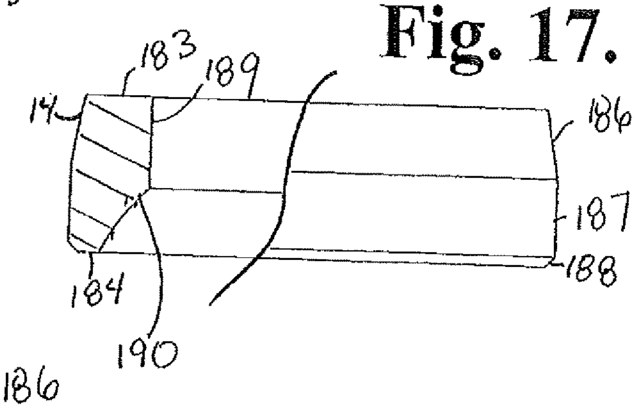
Fig. 18.
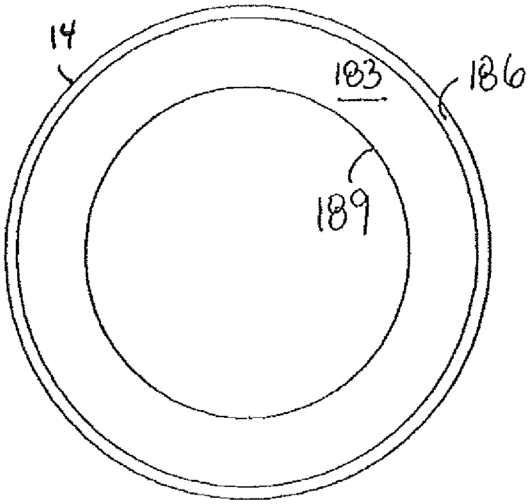
Fig. 19.
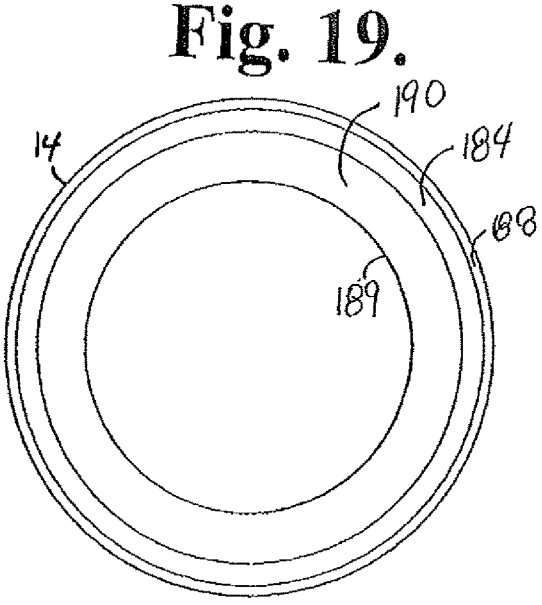
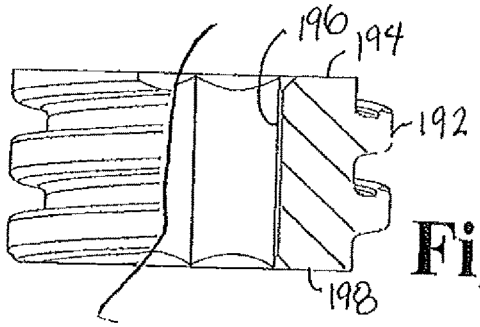
Fig. 20.

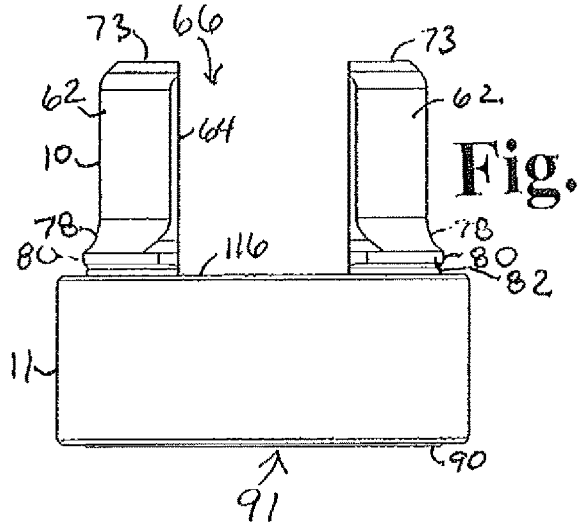
Fig. 21.
Fig. 22.
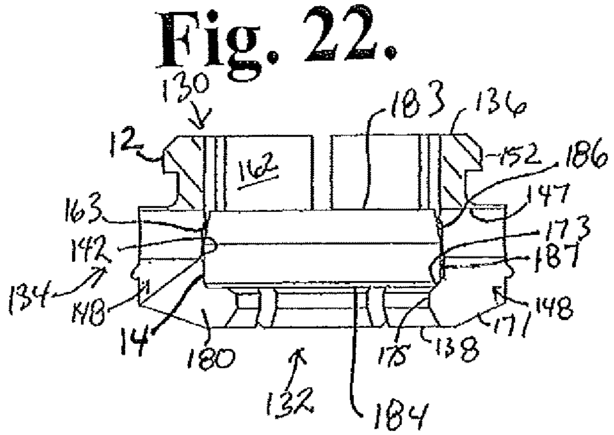
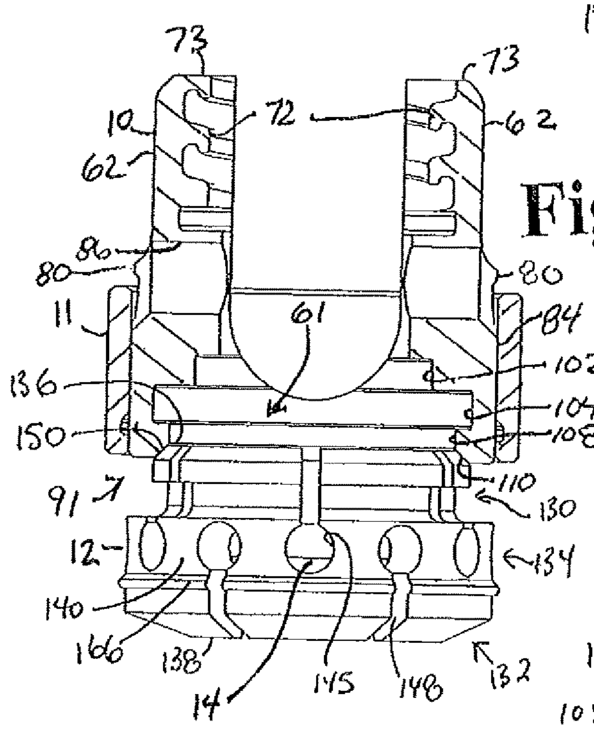
Fig. 23.
Fig. 24.
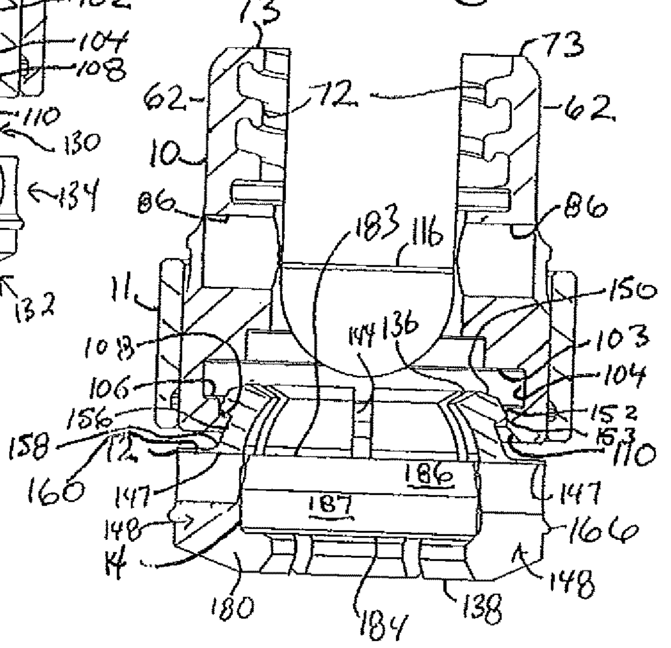

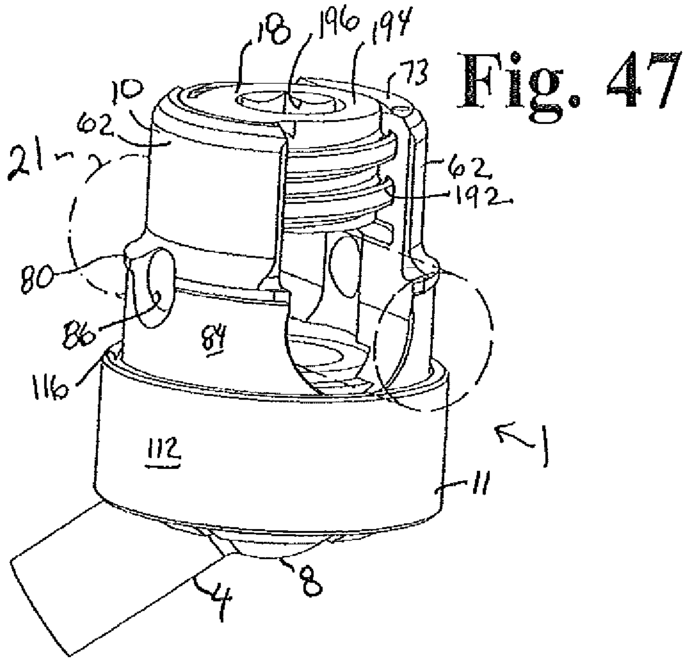
Fig. 47.
Fig. 48.
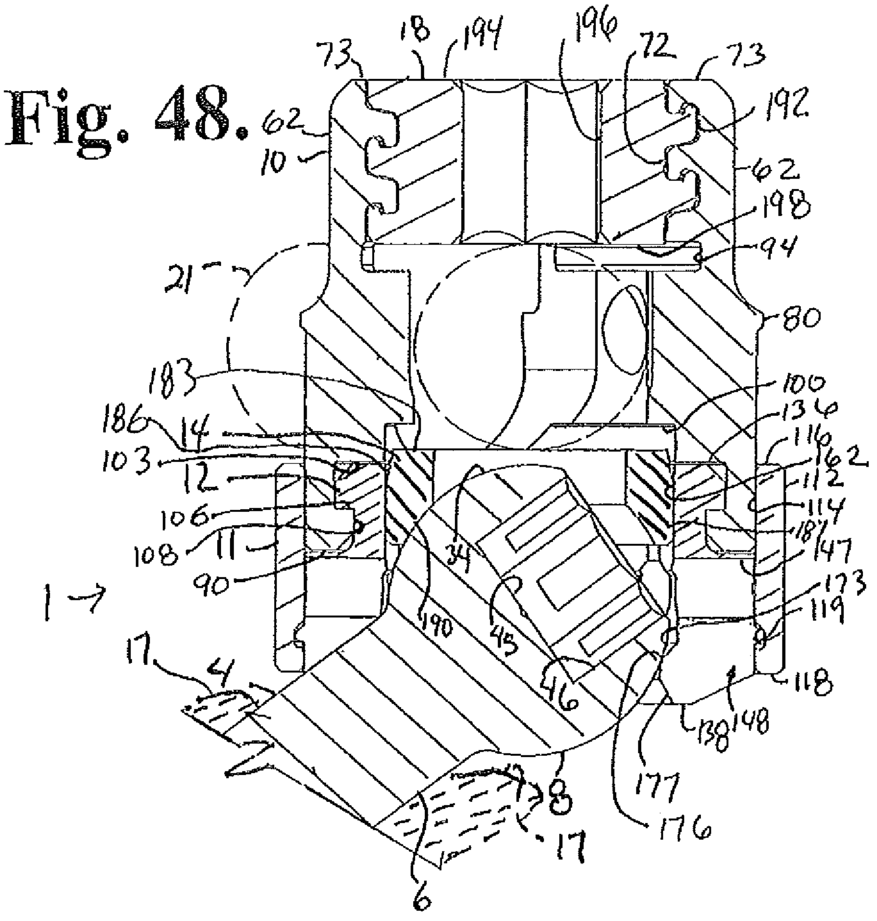

BOTTOM-LOADED PIVOTAL BONE ANCHOR WITH SHANK HEAD COLLET CONTAINMENT

CROSS-REFERENCE TO RELATED APPLICATIONS

This application is a continuation of U.S. application Ser. No. 17/068,530 filed Oct. 12, 2020, which is a continuation of U.S. application Ser. No. 16/724,856 filed Dec. 23, 2019, now 10,806,495, which is a continuation of U.S. application Ser. No. 16/363,041, filed Mar. 25, 2019, now U.S. Pat. No. 10,512,487, which is a continuation of U.S. application Ser. No. 15/420,803 filed Jan. 31, 2017, now U.S. Pat. No. 10,238,430, which is a continuation of U.S. application Ser. No. 14/521,030 filed Oct. 22, 2014, now U.S. Pat. No. 9,566,092, which claims the benefit of U.S. Provisional Application No. 61/896,894 filed Oct. 29, 2013, each of which is incorporated by reference in its entirety herein and for all purposes.

BACKGROUND OF THE INVENTION

The present invention is directed to polyaxial bone anchors for use in bone surgery, particularly spinal surgery and particularly to such bone anchors with compression or pressure inserts and further including retainers for capturing and retaining a bone screw shank head in the receiver member assembly and later fixing the bone screw shank with respect to the receiver assembly.

Bone screws are utilized in many types of spinal surgery in order to secure various implants to vertebrae along the spinal column for the purpose of stabilizing and/or adjusting spinal alignment. When vertebrae of the cervical spine are involved, the connecting structure or structures commonly include a plate and cooperating relatively smaller screws. When the connector is in the form of a rod, both closed-ended and open-ended bone screws are known with open-ended screws being particularly well suited for connections to rods and connector arms because such rods or arms do not need to be passed through a closed bore, but rather can be laid or urged into an open channel within a receiver or head of such a screw. Generally, the screws must be inserted into the bone as an integral unit along with the head, or as a preassembled unit in the form of a shank and pivotal receiver, such as a polyaxial bone screw assembly.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other fixation and stabilization structure.

A common approach for providing vertebral column support is to implant bone screws into certain bones which then in turn support a longitudinal structure such as a rod, or are supported by such a rod. Bone screws of this type may have a fixed head or receiver relative to a shank thereof, or may be of a polyaxial screw nature. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred. Open-ended polyaxial bone screws typically allow for a loose or floppy rotation of the head or receiver about the shank until a desired rotational position of the receiver is achieved by fixing such position relative to the shank during a final stage of a medical procedure when a rod or other longitudinal connecting member is inserted into the receiver, followed by a locking screw or other closure. This floppy feature can be, in some cases, undesirable and make the procedure more difficult, but desirable in other situations.

SUMMARY OF THE INVENTION

An embodiment of the present invention is a bone screw assembly having a shank with an elongate body and a head with a radiused surface, the shank body being configured for fixation to a bone. The assembly further includes a receiver having a top portion and a base with a substantially cylindrical outer surface and a central axis of rotation. The receiver top portion defines a channel for receiving a longitudinal connecting member. The base includes an internal seating surface partially defining a cavity, the top portion channel communicating with the cavity and the cavity communicating with an exterior of the base through a receiver lower opening. The assembly also includes a substantially cylindrical sleeve disposed about and closely receiving the receiver base. The sleeve is axially slidable with respect to the receiver during assembly of the shank with the receiver. A closed retainer cooperating with the receiver and the shank head has a compressible upper portion illustrated with upwardly extending slots, a central band or middle portion and an expandable lower portion illustrated with downwardly extending vertical slots. The retainer upper portion has a first structure engaging the receiver at the internal seating surface. The retainer lower portion is expandable about the shank head and includes a second structure engaging the sleeve to prohibit movement of the sleeve in an axial direction after the shank head is captured by the retainer lower portion. The retainer is attached to the receiver, but rotatable with respect to the receiver prior to fixing of an angle of the shank with respect to the receiver. A compression insert engages both the retainer upper portion and the shank radiused surface. In the illustrated embodiment, when the insert is pressed downwardly into a friction fit engagement with the shank, the retainer upper portion resiliently holds the compression insert into such friction fit engagement with the shank head, allowing for non-floppy pivoting of the shank with respect to the receiver upon the use of some force. In some embodiments, the retainer lower portion includes a cut-out for receiving a portion of the shank and thus providing for an increased pivot angle of the shank with respect to the receiver. Because the retainer can be rotated with respect to the receiver prior to locking of the assembly in a final position, the location of the cut-out may be manipulated during surgery and thus a location of an increased pivot angle of the shank with respect to the receiver may also be manipulated as desired by the surgeon.

Objects of the invention include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 16 is a cross-sectional view taken along the line 16-16 of FIG. 14.

FIG. 17 is an enlarged front elevational view of the insert of FIG. 1 with portions broken away to show the detail thereof.

FIG. 18 is a top plan view of the insert of FIG. 17.

FIG. 19 is a bottom plan view of the insert of FIG. 17.

FIG. 20 is an enlarged front elevational view of the closure top of FIG. 1 with portions broken away to show the detail thereof.

FIG. 21 is an enlarged front elevational view of the receiver and sleeve of FIG. 1 shown in a stage of assembly.

FIG. 22 is an enlarged front elevational view of the retainer and insert of FIG. 1 shown in a stage of assembly and with portions broken away to show the detail thereof.

FIG. 23 is a front elevational view with portions broken away of the receiver and sleeve of FIG. 21 and the retainer and insert of FIG. 22, the retainer being shown in a stage of assembly with the receiver.

FIG. 24 is a front elevational view with portions broken away, similar to FIG. 23 and showing the retainer in a subsequent stage of assembly with the receiver.

FIG. 47 is a reduced perspective view of the assembly of FIG. 45 further shown assembled with a portion of the rod (in phantom) and closure top of FIG. 1, also shown in perspective view.

FIG. 48 is another enlarged view of the assembly of FIG. 47 with portions broken away to show the detail thereof and shown with the shank inserted into bone.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Figure 1:
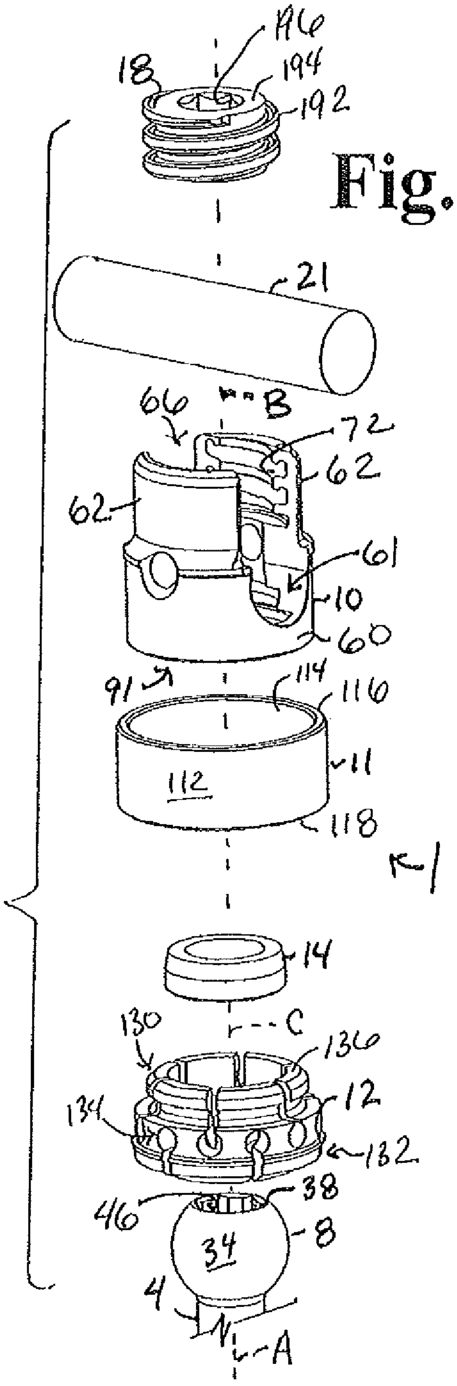
FIG. 1 is an exploded and partial perspective view of a polyaxial bone screw assembly according to an embodiment of the present invention including a shank, a collet-like retainer, a receiver, an outer sleeve and a compression insert and further showing a cooperating rod and closure top.

With reference to FIG. 1, the reference number 1 generally represents a polyaxial bone screw apparatus or assembly according to an embodiment of the present invention that includes a shank 4 that further includes a body 6 integral with an upwardly extending upper portion or head-like capture structure 8; a receiver 10; an outer sleeve 11; a closed collet-like retainer structure 12; and a crown compression or pressure insert 14. The receiver 10, sleeve 11, retainer 12 and compression insert 14 are initially assembled and may be further assembled with the shank 4 either by the vendor or prior to implantation of the shank body 6 into a vertebra 17, as will be described in greater detail below. In some embodiments, the shank could be implanted into a vertebra first, followed by assembly with the other components; however, in the illustrated embodiment of the assembly 1 that is sized and shaped for use on the cervical spine, such a procedure is not preferred due to the small size of both the cervical vertebrae and the assembly 1. FIG. 1 further shows a closure structure 18 for capturing a longitudinal connecting member, for example, a 3.5 millimeter diameter rod 21 which in turn engages the compression insert 14 that presses against the shank upper portion 8 into fixed frictional contact with the retainer 12, so as to capture, and fix the longitudinal connecting member 21 within the receiver 10 and thus fix the member 21 relative to the vertebra 17. The illustrated rod 21 is hard, stiff, non-elastic and cylindrical; however, it is foreseen that in other embodiments, the rod 21 may be elastic, deformable and/or of a different cross-sectional geometry. In some embodiments, the bone screw assembly 1 may also cooperate with soft connecting systems, such as spinal connectors having rigid sleeves for placement within bone screw receivers in lieu of a rod, such sleeves including through bores for receiving a tensioned cord, for example. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure. The drawings at FIGS. 37-43 also illustrate a driver, generally 24 for use with the assembly 1 as will be described in greater detail below.

Figure 2:
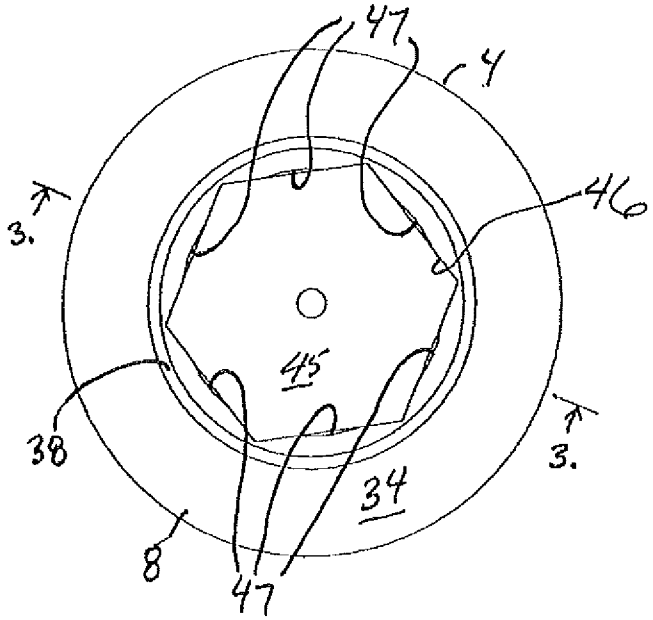
FIG. 2 is an enlarged top plan view of the shank of FIG. 1.
Figure 3:
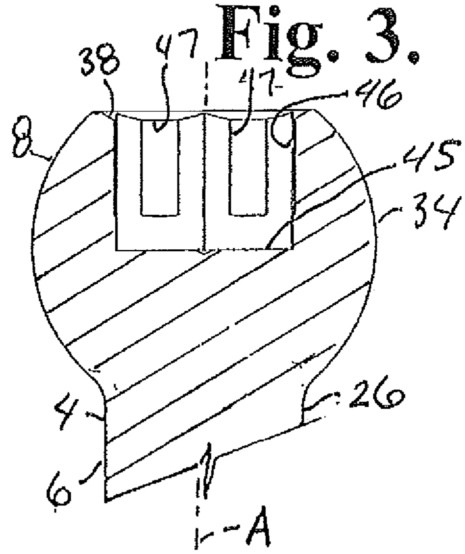
FIG. 3 is reduced and partial cross-sectional view taken along the line 3-3 of FIG. 2.
Figure 4:
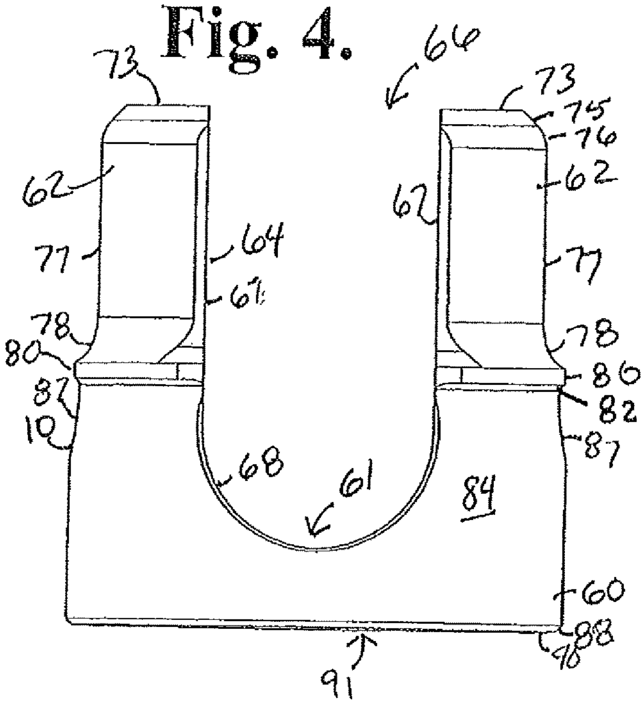
FIG. 4 is an enlarged front elevational view of the receiver of FIG. 1.
Figure 5:
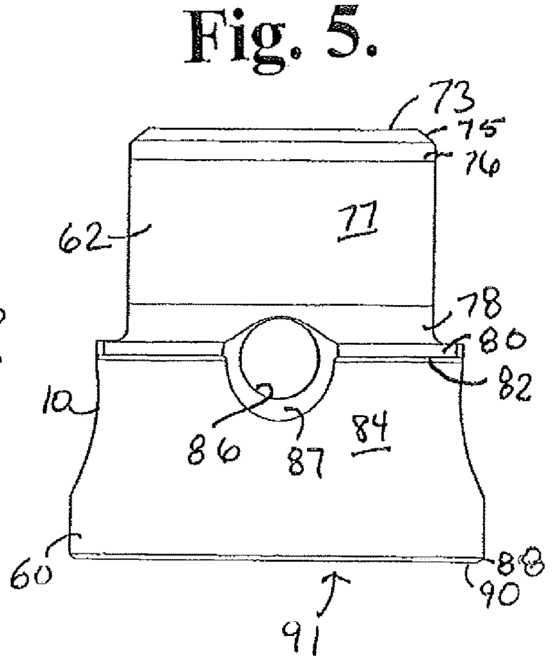
FIG. 5 is a side elevational view of the receiver of FIG. 4.
Figure 6:
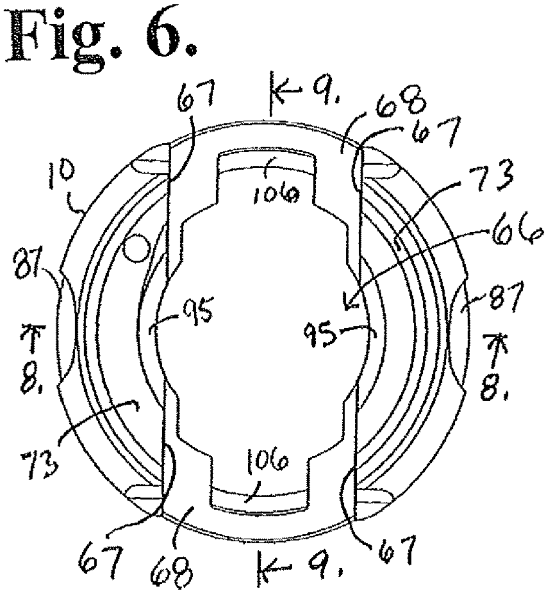
FIG. 6 is a top plan view of the receiver of FIG. 4.
Figure 7:
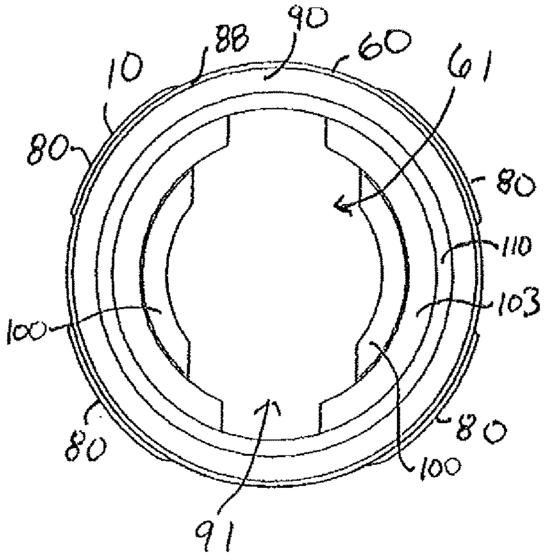
FIG. 7 is a bottom plan view of the receiver of FIG. 4.
Figure 8:
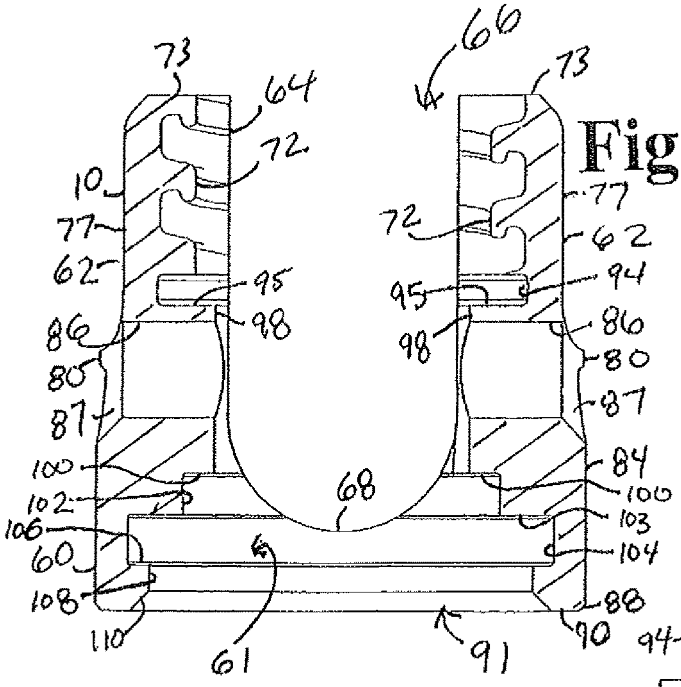
FIG. 8 is an enlarged cross-sectional view taken along the line 8-8 of FIG. 6.
Figure 9:
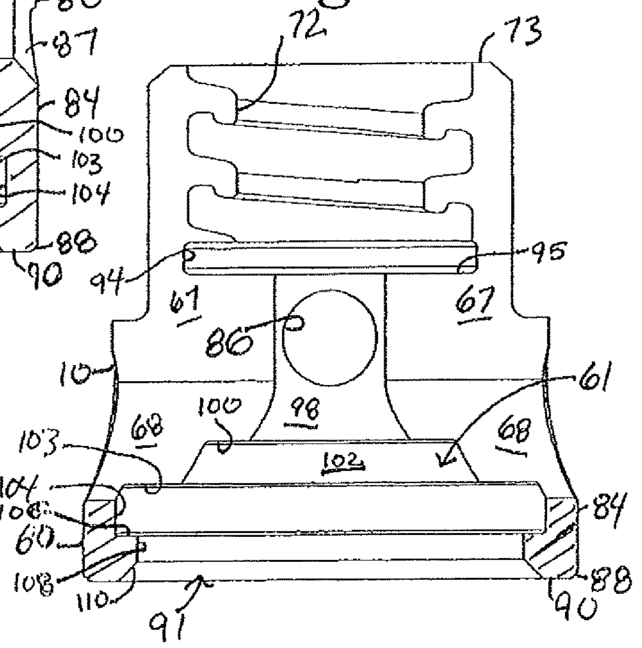
FIG. 9 is an enlarged cross-sectional view taken along the line 9-9 of FIG. 6.

The shank 4, best illustrated in FIGS. 1-3, is elongate, the shank body 6 being only partially shown in FIGS. 1 and 3. The body 6 is elongate and further includes one or more helically wound threads for bone engagement that are known in the art of pedicle screws, in particular smaller screws sized and shaped for use on the cervical spine. An example of a larger pedicle screw shank for use with some embodiments of the invention is illustrated, for example, in U.S. Pat. No. 6,726,689, which is also incorporated herein by reference as an example of flange form guide and advancement structures for use with receivers 10 and closures 18 of embodiments of the invention. During use, the body 6 utilizing the thread or threads (not shown) for gripping and advancement is implanted into the vertebra 17 (e.g., see FIG. 48) leading with a tip of the shank 6 and driven down into the vertebra with an installation or driving tool (not shown), so as to be implanted in the vertebra to a location at or near a neck thereof, as more fully described in the paragraphs below. The shank 4 has an elongate axis of rotation generally identified by the reference letter A.

A neck 26 extends axially upward from the shank body 6. The neck 26 may be of the same or of a slightly reduced radius as compared to an adjacent upper end or top of the body 6 where the thread or threads terminate. Extending axially and outwardly from the neck 26 is the shank upper portion or head 8 that provides a connective or capture apparatus disposed at a distance from the threaded portion of the shank 6 and thus at a distance from the vertebra 17 when the body 6 is implanted in such vertebra.

The shank upper portion 8 is configured for a fixed engagement between the portion 8 and the retainer 12 and a pivotable connection between the shank 4 and the receiver 10 prior to fixing of the shank 4 in a desired position with respect to the receiver 10. The shank upper portion 8 has an outer, convex and substantially spherical surface 34 that extends outwardly and upwardly from the neck 26 and terminates at an annular top or rim surface 38. The rim 38 may be planar, or as in the illustrated embodiment sloping downwardly and inwardly and towards the axis A. The spherical surface 34 has an outer radius configured for frictional sliding and then ultimate fixed cooperation with a concave surface of the compression insert 14 and concave surfaces of the retainer 12 as will be discussed more fully in the paragraphs below. In some embodiments the top surface 38 may be substantially perpendicular to the axis A. The spherical surface 34 shown in the present embodiment is substantially smooth, but in some embodiments may include a roughening or other surface treatment. The shank spherical surface 34 is locked into place exclusively by the insert 14 and the retainer 12 and not by inner surfaces defining the receiver cavity, the shank being held in spaced relation with the receiver by the retainer 12.

A counter sunk substantially planar base 45 partially defines an internal drive feature or imprint 46. The illustrated internal drive feature 46 is an aperture formed in the top surface 38 and generally has a hex shape designed to receive a driving tool of an Allen wrench type, such as the driver 24, into the aperture for rotating and driving the bone screw shank 4. Each of the six faces of the drive 46 also includes a shallow indentation or groove that has a cylindrical surface 47 that begins at or near the rim 38 and terminates at a location spaced from the drive base 45. It is foreseen that the drive 46 tool engagement structure may take a variety of tool-engaging forms and may include one or more apertures of various shapes, such as a pair of spaced apart apertures or a multi-lobular or star-shaped aperture, such as those sold under the trademark TORX, or the like. The seat or base surface 45 of the drive feature 46 is disposed substantially perpendicular to the axis A with the drive feature 46 otherwise being coaxial with the axis A. The drive seat 45 may include beveled or stepped surfaces that may further enhance gripping with the driving tool. In operation, a driving tool is received in the internal drive feature 46, being seated at the base 45 and engaging the plurality of faces of the drive feature 46 for both driving and rotating the shank body 6 into the vertebra 17, either before the shank 4 is attached to the receiver 10 (in larger embodiments useful for thoracic or lumbar spine applications) or, as in the present embodiment, after the shank 4 is attached to the receiver 10, with the shank body 6 being driven into the vertebra 17 with the driving tool extending into the receiver 10.

The shank 4 shown in the drawings is solid, but in some embodiments may be cannulated, having a small central bore extending an entire length of the shank 4 along the axis A. Such a bore is typically defined by an inner cylindrical wall of the shank 4 having a circular opening at the shank driving tip and an upper opening communicating with the external drive 46 at the driving seat 45. Such a bore is typically coaxial with the threaded body 6 and the upper portion 8. Such a bore provides a passage through the shank 4 interior for a length of wire (not shown) inserted into the vertebra 17 prior to the insertion of the shank body 6, the wire providing a guide for insertion of the shank body 6 into the vertebra 17.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$, tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 4-9, the receiver 10 has a generally U-shaped appearance with various discontinuous and continuous cylindrical inner and outer profiles. The receiver 10 has a central axis of rotation B that is shown in FIG. 1 as being aligned with and the same as the axis of rotation A of the shank 4, such orientation being desirable during assembly of the receiver 10, retainer 12 and insert 14 with the shank 4. After the receiver 10 is pivotally attached to the shank 4, the axis B is typically disposed at an angle with respect to the axis A, as shown, for example, in FIGS. 44-46.

The receiver 10 includes a base or lower body portion 60 that is illustrated as having a cylindrical outer surface, that in some embodiments may include other outer surface geometries, including curved, frusto-conical and partially planar. The base 60 defines a bore or inner cavity, generally 61, the base 60 being integral with a pair of opposed upstanding arms 62 forming a cradle and defining a channel 64 between the arms 62 with an upper opening, generally 66, the channel further defined by substantially planar interior arm surfaces 67 that extend downwardly and transition to a U-shaped lower saddle or seat 68, the channel 64 having a width for operably snugly receiving the rod 21 or portion of another longitudinal connector between the arms 62; the channel 64 communicating with the base cavity 61.

Each of the arm interior surfaces 67 have formed or machines therein various inner cylindrical profiles, an upper one of which is a partial helically wound guide and advancement structure 72 located adjacent a top surface or rim 73 of each of the arms 62. In the illustrated embodiment, the guide and advancement structure 72 is a partial helically wound interlocking flangeform configured to mate under rotation with a similar structure on the closure structure 18, as described more fully below. However, it is foreseen that for certain embodiments of the invention, the guide and advancement structure 72 could alternatively be a square-shaped thread, a buttress thread, a reverse angle thread or other thread-like or non-threadlike helically wound discontinuous advancement structures, for operably guiding under rotation and advancing the closure structure 18 downward between the arms 62, as well as eventual torquing when the closure structure 18 abuts against the rod 21 or other longitudinal connecting member. It is foreseen that the arms could have break-off extensions.

With respect to the outer surfaces of the receiver 10, near each arm top surface 73, an outwardly and downwardly extending frusto-conical surface 75 transitions to an outer curved surface 76 that terminates at an outer discontinuous cylindrical surface 77, the surface 77 extends along a majority of each arm 62 and terminates at a curved, outwardly flaring surface 78. The surface 78 terminates at a narrow cylindrical surface 80. The surface 80 terminates at an overhang or ledge 82 that extends inwardly to a cylindrical surface 84 that is contiguous with the cylindrical base 60. The cylindrical surface 84 has a diameter that is greater than a diameter of the discontinuous cylindrical surface 80. The cylindrical surface 80 has a diameter that is greater than a diameter of the discontinuous surface 77. The cylindrical surface 84 (as well as the cylindrical surface 80 and the surface 78) is discontinuous at and near the ledge 82, separated by the u-shaped channel 64 as well as by opposed through bores 86, each bore 86 located centrally in one of the arms 62 and extending between the surfaces 78, 80, 82 and 84 at an outer opening thereof and the inner arm planar surface 67 at an inner opening thereof. The bores 86 may further include one or more curved or tapered surfaces 87 that transition onto each arm outer surface. The opposed bores 86 may be used with tools for holding the receiver 10 during assembly with the other components of the bone anchor and during implantation and manipulation of the assembly 1 during surgery, for example. It is foreseen that other tool receiving grooves, depressions or apertures may be configured in a variety of shapes and sizes and be disposed at other locations on the receiver arms 62. At the base 60, the cylindrical surface 84 terminates at a bevel 88 that transitions to a planar annular base bottom surface 90 that partially defines an opening, generally 91 into the receiver cavity 61.

Returning to the interior surface 67 of the receiver arms 62, located below the guide and advancement structure 72 is a discontinuous cylindrical surface 94 partially defining a run-out feature for the guide and advancement structure 72.

The cylindrical surface 94 has a diameter equal to or slightly greater than a greater diameter of the guide and advancement structure 72. Moving downwardly in a direction toward the base 60, adjacent the cylindrical surface 94 of each arm is a run-out seat or surface 95 that extends inwardly toward the axis B and is substantially perpendicular to the axis B. In other embodiments, the surface 95 may gently slope downwardly toward the axis B. Adjacent to and located below the surface 95 and formed in the planar surface 67 and the saddle surface 68 of each arm in an area near and surrounding about the through bore 86 is a shallow cylindrical surface 98 that terminates at a ledge or ceiling surface 100 of each arm, the surface 100 substantially perpendicular to the axis B and extending outwardly away from the axis B. Extending downwardly from the ceiling surface 100 of each arm is another cylindrical surface 102 that is also discontinuous, being separated by the saddle portion 68 that partially forms the channel 64. The cylindrical surface 102 of each arm terminates at a discontinuous annular ledge or ceiling surface 103 that extends outwardly away from the axis B that in turn terminates at a cylindrical surface 104 that extends below the u-shaped channel saddle 68 and thus has a continuous portion formed in the base 60 and thus underneath both of the arms 62. The cylindrical surface 104 terminates at a continuous annular seating surface 106 that extends inwardly toward the axis B and is substantially perpendicular thereto. The surface 106 terminates at another cylindrical surface 108. The cylindrical surface 104 has a diameter greater than a diameter of the cylindrical surface 102 and also greater than a diameter of the cylindrical surface 108. The surface 108 diameter is greater than the surface 102 diameter. The cylindrical surface 108 terminates at an outwardly flaring frusto-conical surface 110 that terminates at the base surface 90, the surfaces 110 and 90 forming the lower opening 91 of the receiver cavity 61.

Figure 10:
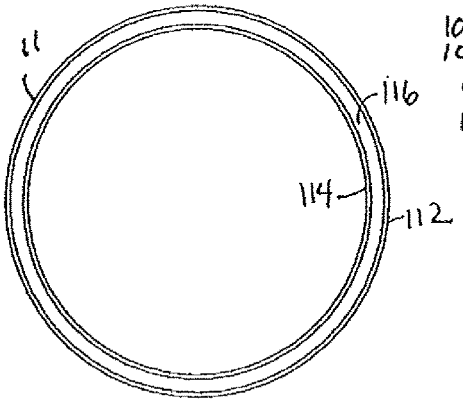
FIG. 10 is an enlarged top plan view of the sleeve of FIG. 1.
Figure 11:
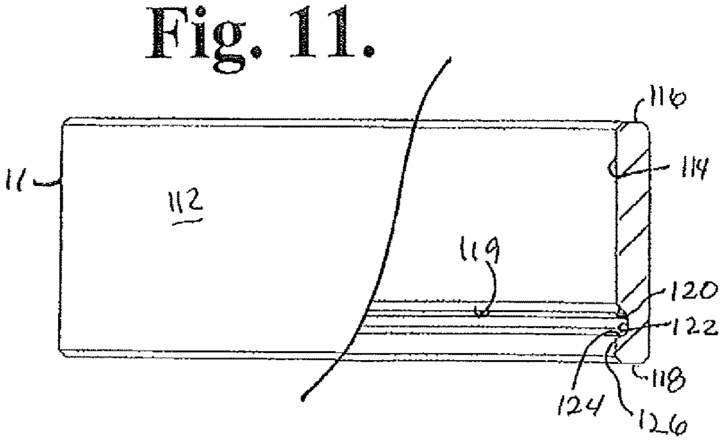
FIG. 11 is an enlarged front elevational view of the sleeve of FIG. 10 with portions broken away to show the detail thereof.
Figure 12:
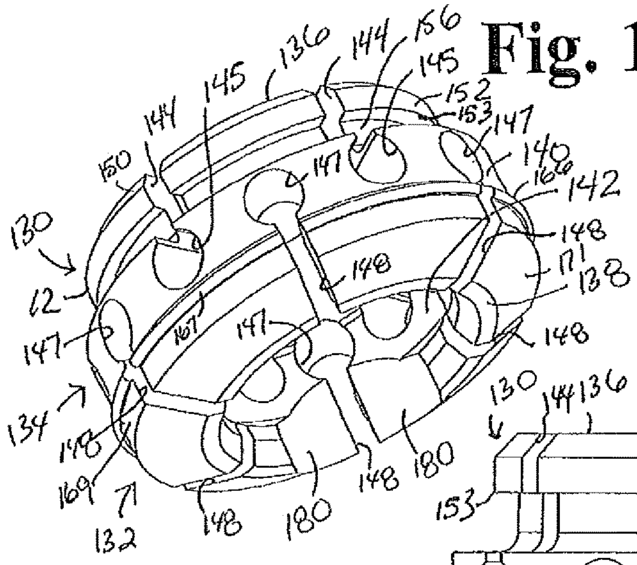
FIG. 12 is an enlarged perspective view of the retainer of FIG. 1.
Figure 13:
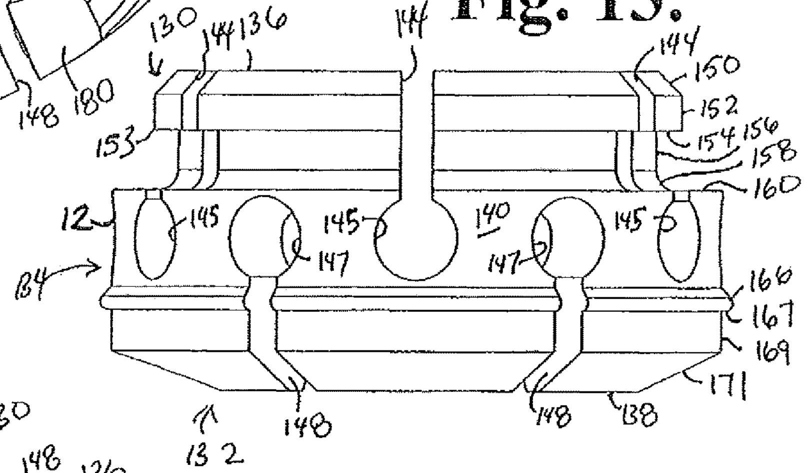
FIG. 13 is an enlarged front elevational view of the retainer of FIG. 12.
Figure 14:
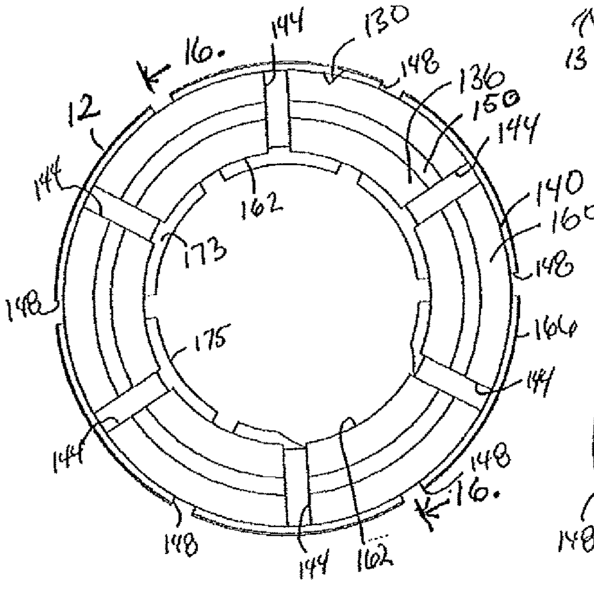
FIG. 14 is a top plan view of the retainer of FIG. 12.
Figure 15:
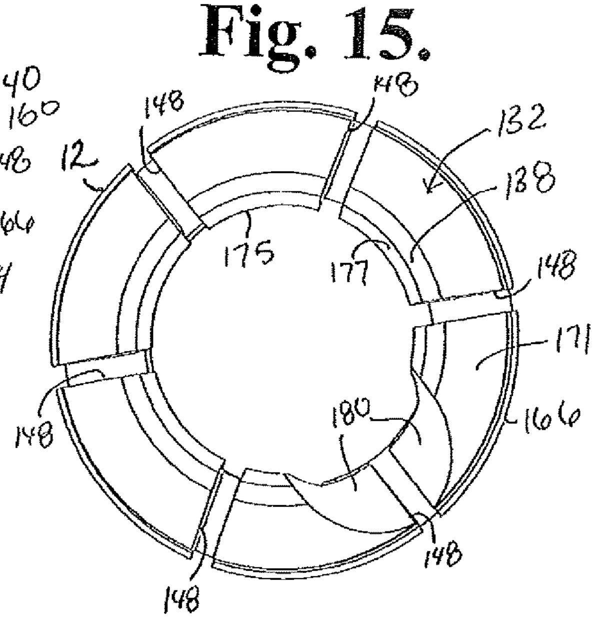
FIG. 15 is a bottom plan view of the retainer of FIG. 12.

With particular reference to FIGS. 1 and 10-11, the sleeve 11 that is received over the outer cylindrical surface 84 of the receiver at the base 60 thereof is a substantially tubular structure having a substantially uniform outer cylindrical surface 112, and inner cylindrical surface 114, an annular and planar top surface 116 and an annular and planar bottom surface 118, the top and bottom surfaces 116 and 118 both being substantially perpendicular to the outer and inner cylindrical surfaces 112 and 114. In operation the sleeve 11 has the same central axis of rotation B as the receiver 10. Near the bottom surface 118 and adjacent to the surface 114 is an inner groove, generally 119, substantially defined by an outwardly and downwardly sloping surface 120, a cylindrical surface 122 and a bottom annular seating surface 124. The surface 124 terminates at a lower cylindrical surface 126 having a diameter equal to the cylindrical surface 114. The surface 126 terminates at or near the bottom annular surface 118. In the illustrated embodiment, beveled surfaces are located on either side of the top surface 116 and on either side of the bottom surface 118. The inner surfaces 120, 122 and 124 that define an inner cylindrical recess or groove 119 may also be connected by angled or beveled surfaces. The surfaces 120, 122 and 124 cooperate with an outer lip of the retainer 12 as will be described in greater detail below. The diameter of the surfaces 114 and 126 is slightly larger than a diameter of the cylindrical surface 84 of the receiver 10 so that the sleeve 11 is closely, slidingly received by the inner surfaces 114 and 126 of the sleeve during assembly.

With particular reference to FIGS. 1 and 12-16, the rotatable collet-like retainer 12 generally forms a closed ring but is expandable and contractible at both an upper portion and a lower portion thereof and thus may be described as having an upper resilient portion, generally 130, and a lower resilient portion, generally 132, both portions integral with a central band, generally 134. Both portions 130 and 132 have vertical slots and communicating cylindrical bores that result in key-hole-like openings that open upwardly for the portion 130 and open downwardly for the portion 132 to provide for substantially independent expandability and contractibility of both the upper and lower portions 130 and 132 with respect to the central band 134 during various steps of assembly with the receiver 10, sleeve 11, shank 4 and insert 14. The portions 130 and 132 and the central band 134 are integral to one another, resulting in a one-piece retainer having discontinuous surfaces that is also rotatably engaged to the receiver 10 and pivotally engaged to the shank head 8 as will be described in greater detail below. When assembled with the receiver 10, the retainer 12 has a central axis C that is the same as the central axis of rotation B of the receiver 10. The upper portion 130 has outer structure for engagement with inner surfaces of the receiver 10 as will be described in greater detail. The lower portion 132 has inner structure for capturing the shank head 8 within the retainer central portion 134 and ultimately fixing the shank head 8 against inner surfaces or edges of the lower portion 132. The lower portion further includes an outer lip that engages the outer sleeve 11, the sleeve 11 providing a hard outer structural support to the lower portion 132 preventing expansion of the lower portion 132 after the shank head 8 is positioned within the retainer 12 as will be described in greater detail below.

When in a neutral state, the retainer 12 has a substantially planar and annular discontinuous top surface 136 and an opposed and parallel substantially planar and annular discontinuous bottom surface 138. The central band 134 includes a substantially cylindrical outer surface 140 and a substantially cylindrical inner surface. Formed in the top surface 136 and extending into the central band portion are six equally spaced vertical slots 144, each slot communicating with and terminating at a circular through bore 145 than runs between the surfaces 140 and 142 of the central band portion 134. The slots 144 run parallel to the central axis C of the retainer 12. The through bores 145 run radially toward the axis C. Between each through bore 145 is an identically shaped through bore 147 that communicates with a vertical slot 148 that runs downwardly toward and through the retainer bottom surface 138. Thus, there are also six vertical slots 148 and six communicating through bores 147. The vertical slots 148 of the lower portion 132 also run parallel to the axis C and the through bores 147 run radially thereto. In the illustrated embodiment there are six upper slots 144 and communicating through bores 145 and six lower slots 148 and communicating through bores 147. However, it is foreseen that greater or fewer numbers of slots and through bores may be used in other embodiments of the invention, depending in part on the material used for the retainer 12 which in the illustrated embodiment, preferred materials include titanium alloy and cobalt-chrome alloy. Harder materials such as certain cobalt chrome alloys may require more slots and communicating key-hole through bores than will softer, more resilient materials such as titanium, titanium alloy or stainless steel.

Returning to the retainer upper portion 130 that is sized and shaped to resiliently engage and fix to the receiver 10 as will be described in greater detail below, the vertical slots 144 also extend through the following outer surfaces of the portion 130: a frusto-conical outer surface 150 that is adjacent the top surface 136 and terminates at an outer cylindrical surface 152 having a lower circular edge 153; an annular ledge 154 that runs from the edge 153 of the outer cylindrical surface 152 and terminates at another cylindrical surface 156, the surface 156 having a diameter that is smaller than a diameter of the cylindrical surface 152; and an outwardly flaring curved surface 158 that transitions to an annular surface 160 that terminates at the mid-portion or band outer surface 140. The surfaces 160 and 154 are both substantially perpendicular to the axis C when the retainer 12 is in a neutral position. The retainer surfaces 136, 152 and 154 are sized and shaped for sliding rotational engagement with the surfaces 103, 104 and 106 as will be described in greater detail below. The retainer 12 includes an inner cylindrical surfaces 162 running from the top surface 136 to an inner bevel 163 that transitions radially outwardly to the inner band surface 142. The inner surfaces 162 is sized to closely receive an outer surface of the insert 14 during assembly as will be described in greater detail below. All of the surfaces 150, 152, 154, 156, 158, 160, 162 and 163 are discontinuous because the vertical slots 144 run therethrough. The through bores 145 that communicate with the slots 144 as well as the through bores 147 that are formed in and through the outer and inner central band surfaces 140 and 142, respectively, also extend through a portion of the inner cylindrical surface 162 and the bevel 163 as best shown in FIG. 16.

The retainer lower portion 132 is defined by the following features described as they appear when the retainer 12 is in a neutral state: an outer discontinuous lip 166 that extends radially outwardly and downwardly from the central band outer surface 140 and then transitions inwardly to form a lower ledge surface 167 that terminates at a cylindrical surface 169. When the retainer 12 is in a neutral state, the cylindrical surface 169 has a diameter that is the same or substantially close to the diameter of the surface 140. The cylindrical surface 169 extends to a lower inwardly radially extending discontinuous frusto-conical surface 171 that terminates at the bottom surface 138. The outer lip 166 is sized and shaped to be ultimately received within the inner groove 119 of the sleeve 11. Adjacent the central band portion inner cylindrical surface 142, is a radially inwardly extending surface 173 that terminates at an inner cylindrical surface 175, the surface 175 being substantially parallel to the axis C when the retainer 12 is in a neutral state. A discontinuous circular edge 176 is formed by a juncture of the surfaces 173 and 175, the edge 176 ultimately is in locked frictional engagement with the spherical surface 34 of the shank head 8 as will be described in greater detail below. The cylindrical surface 175 terminates at a radially outwardly flaring frusto-conical surface 177 that terminates at the bottom surface 183. Formed or cut-out of the lower surfaces 138, 171 and 177 and positioned centrally at a slot 148 is a discontinuous curved surface 180 sized and shaped to receive a portion of the shank body 6 to provide for an extended angle of pivot as shown, for example in FIG. 45 and described in greater detail below. The retainer lower portion 132 outer and inner surfaces 166, 167, 169, 171, 173, 175, 177 and 180 are all discontinuous, being separated by the six lower vertical slots 148 that each communicate with one of the through bores 147. None of the through bores 147 extend downwardly into the lower portion 132. All of the through bores 145 and 147 are located substantially in the central portion or band 134 and include a small upper part thereof partially located in the retainer upper portion 130. The bores 145 and 147 are evenly and uniformly aligned in a circle that surrounds the axis C and only differ from each other by a direction of an opening thereof that communicates with either an upwardly or downwardly directed slot 144 or 148.

With particular reference to FIGS. 1 and 17-19, the crown compression or pressure insert 14 is illustrated that is sized and shaped to be received by and down-loaded through the retainer 12 upper portion and temporarily seated within the central band 134 prior to assembly of the retainer 12 upper portion 130 with the receiver 10 at the receiver lower opening 91. The compression insert 14 is sized and shaped to be ultimately received in the retainer upper portion 130 as will be described in greater detail below. The compression insert 14 has an operational central axis that is the same as the central axis B of the receiver 10. Prior to operation, the insert 14 may be advantageously manipulated downwardly into a friction fit with the shank head 8 wherein the insert 14 frictionally engages the bone screw shank upper portion spherical surface 34, but is not locked against the portion 8, (i.e., movement occurs when some force is applied) allowing for a non-floppy movement and placement of the shank 4 with respect to the receiver 10 at a desired angle during surgery prior to locking of the shank with respect to the receiver near the end of the procedure.

The compression insert 14 is substantially cylindrical and tubular and includes a planar annular top surface 183 and a planar annular bottom surface 184, the surfaces 183 and 184 being perpendicular to the central axis of rotation. A radially outwardly extending frusto-conical surface 186 begins at the top surface 183 and terminates at an outer cylindrical surface 187. The surface 187 extends from the surface 186 to an outer beveled surface 188 that transitions inwardly to the bottom annular surface 184. An inner cylindrical surface 189 extends from the top surface 183 and terminates at a radiused surface 190, the surface 190 terminating at the insert bottom surface 184. The surface 190 is substantially spherical and sized to closely receive and engage the spherical surface 34 of the shank head 8. Thus, a radius of the surface 190 is approximately the same of substantially close to a radius of the spherical surface 34.

The surfaces 186 and 187 are sized and shaped to generally fit within the retainer inner band surface 142 and retainer top portion discontinuous inner surface 162. In a final operational position, the outer cylindrical surface 187 fits closely within the retainer inner surface 162 as will be described in more detail below.

The insert inner cylindrical surface 189 and spherical surface 190 define a bore sized and shaped to receive the driver 24 therethrough that engages the shank drive feature 46 during assembly and also when the shank body 6 is driven into bone with the receiver 10 attached. Also, the bore may receive other manipulation tools.

With reference to FIGS. 1 and 47-50, for example, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface of uniform diameter. The illustrated rod 21 is sized for use on the cervical spine and thus has a diameter of 3.5 mm and may have a diameter as small as 3.0 mm. The rod 21 may be made from a variety of metals, including hard and soft metal alloys and hard and soft or deformable and less compressible plastics, including, but not limited to rods made of elastomeric, polyetheretherketone (PEEK) and other types of materials.

In other embodiments, it is foreseen that longitudinal connecting members for use with the assembly 1 may take a variety of shapes, including but not limited to rods or bars of oval, rectangular or other curved or polygonal cross-section. Some other embodiments may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 or the compression insert of larger polyaxial screws for the thoracic or lumbar spine of a cooperating receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies, for example. A damping component or bumper may be attached to the longitudinal connecting member at one or both sides of the bone screw assembly. A rod or bar (or rod or bar component) of a longitudinal connecting member may be made of a variety of materials ranging from soft deformable plastics to hard metals, depending upon the desired application. Thus, bars and rods may be made of materials including, but not limited to metal and metal alloys including but not limited to stainless steel, titanium, titanium alloys and cobalt chrome alloys; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1, 20 and 47-50, the closure structure or closure top 18 shown with the assembly 1 is rotatably received between the spaced arms 62 of the receiver 10. It is noted that the closure 18 top could be a twist-in or slide-in closure structure. The illustrated closure structure 18 is substantially cylindrical and includes an outer helically wound guide and advancement structure 192 in the form of a flange that operably joins with the guide and advancement structure 72 disposed on the arms 62 of the receiver 10. The flange form utilized in accordance with embodiments of the present invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 18 downward between the arms 62 and having such a nature as to resist splaying of the arms 62 when the closure structure 18 is advanced into the channel 64, the flange form illustrated herein as described more fully in Applicant's U.S. Pat. No. 6,726,689 is preferred as the added strength provided by such flange form beneficially cooperates with and counters any reduction in strength caused by the small size of the cervical screw and longitudinal connecting member. A single start flange form 192 is illustrated; however, it is foreseen the closure 18 may have two starts with cooperating flange form structure on the receiver arms 62. The illustrated closure structure 18 also includes a top surface 194 with an internal drive 196 in the form of an aperture that is illustrated as a hex-shaped internal drive, or may be, for example, a star-shaped or Torx drive, or other internal drives such as slotted, tri-wing, spanner, two or more apertures of various shapes, and the like. A driving tool (not shown) sized and shaped for engagement with the internal drive 196 is used for both rotatable engagement and, if needed, disengagement of the closure 18 from the receiver arms 62. It is also foreseen that the closure structure 18 may alternatively include a break-off head designed to allow such a head to break from a base of the closure at a preselected torque, for example, 30 to 60 inch pounds. Such a closure structure would also include a base having an internal drive to be used for closure removal. The drive extends all the way through the closure to a bottom surface 198 of the closure and may include a rim or a point and rim in some embodiments. The drive provides a cannulation through bore extending along a central axis thereof and through the top and bottom surfaces thereof. Such a through bore provides a passage through the closure 18 interior for a length of wire (not shown) inserted therein to provide a guide for insertion of the closure top into the receiver arms 62 in some embodiments and methods.

In the illustrated embodiment, the receiver 10 is preferably made from titanium or titanium alloy as titanium is easier to machine than a harder material such as cobalt chrome. Also, the sleeve 11 helps to provide strength and stability to the overall assembly 1. The sleeve 11, retainer 12 and crown insert 14 may each be made from a variety of materials including cobalt chrome alloys, titanium and titanium alloys.

The two-piece driving tool 24 illustrated in FIGS. 37-43 for placing the insert 14 into friction fit relationship with the shank head 8 and later driving the shank 4 into the vertebra 17 includes an inner plunger/driver 210 in slidable relationship with an outer holder/receiver engagement tool 212. The inner plunger/driver 210 includes an upper holding potion that further includes a cylindrical holding portion 215 and a faceted end portion 217 having four sides and a square planar end surface 218. The cylindrical portion 215 is integral with a lower cylindrical portion 220 having a diameter smaller than a diameter of the portion 215. The portion 220 terminates at a radially outwardly extending lip 222 having an annular planar surface 223. Extending from the surface 223 is a hex-shape drive 224 having six faces and a planar tip or end surface 226. The drive 224 is sized and shaped to be closely received by the shank drive 46.

The outer holder 212 includes an annular planar end surface 228 adjacent a holding portion 230 that curves inwardly near a center thereof and is substantially wider than the driver portion 215 diameter. In other words an outer diameter defined by the holding portion 230 is greater than the diameter of the portion 215. The portion 230 terminates at a lower planar annular surface 232. A cylindrical surface 234 extends downwardly from the surface 232. The surface 234 has a diameter smaller than the diameter of the cylindrical portion 215. Near an end 236 of the portion 234 a helically wound guide and advancement structure 238 is formed on the portion 234 that is sized and shaped to helically mate with the receiver helical guide and advancement structure 72. A cylindrical surface 240 located below the guide and advancement structure terminates at an annular end surface 241. The outer holder 212 is tubular having an inner cylindrical surface 244 running from the top end surface 228 to the bottom annular surface 241, the surface 244 sized and shaped to closely slidingly receive the inner plunger driver 210 at the cylindrical surface 220. Operation of the tool 24 will be described in greater detail below.

With reference to FIGS. 21-36, the receiver 10, sleeve 11, retainer 12 and insert 14 are preferably assembled at a factory setting that includes tooling for holding and alignment of the component pieces as well as compressing or expanding upper and lower portions 130 and 132 of the retainer. In some circumstances, the shank 4 is also assembled with the receiver 10, sleeve 11, retainer 12 and compression insert 14 at the factory. In other instances, it may be more desirable for the surgical staff to pre-assemble a shank of a desired size and/or variety (e.g., surface treatment of roughening the upper portion 8 and/or hydroxyapatite on the shank 6), with the receiver, sleeve, retainer and compression insert. Allowing the surgeon to choose the appropriately sized or treated shank 4 advantageously reduces inventory requirements, thus reducing overall cost. Although it may be possible to implant the shank 4 into a vertebra first, followed by pressing the retainer (that is already attached to the receiver) over the shank, this may not be desirable due to the extremely small size of the assembly 1 and the more fragile nature of the smaller cervical spine vertebrae for which the assembly 1 is designed.

Pre-assembly of the receiver 10 with the sleeve 11 is shown in FIG. 21. The outer sleeve 11 is placed below the receiver 10 as shown in the exploded view of FIG. 1 and the receiver base is dropped into the sleeve until the sleeve top surface 116 abuts against the overhang 82 located beneath the cylindrical surface 80. The sleeve inner surface 114 is in slidable rotatable engagement with the receiver base outer surface 84. The sleeve 11 can also be slid axially downwardly off of the receiver base 60 at this time.

Pre-assembly of the retainer 12 and the insert 14 is shown in FIG. 22. The insert 14 is inserted into the retainer 12 with the insert 14 bottom surface 184 initially facing the retainer top surface 136. The insert 14 is then dropped or moved within the retainer inner discontinuous surface 162 and then the retainer inner central band surface 142 in a co-axial manner until the bottom surface 184 of the insert 14 rests on the retainer lower portion inner surface 173 as shown in FIG. 22. Now the retainer 12 with captured insert 14 is ready to be assembled with the receiver 10.

Figure 25:
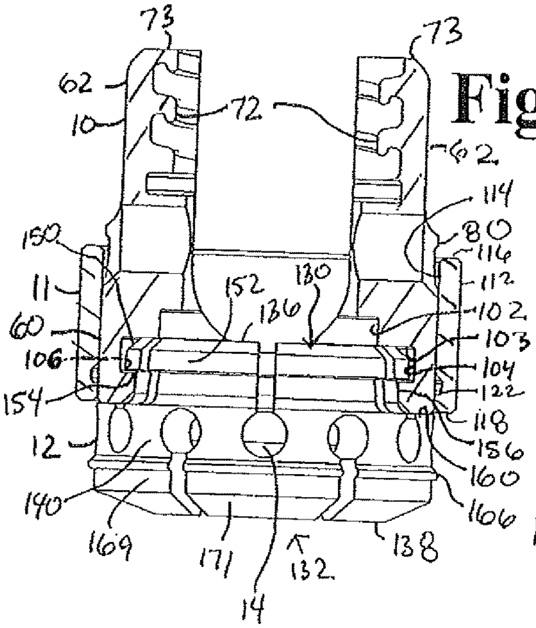
FIG. 25 is a front elevational view with portions broken away, similar to FIG. 24 and showing the retainer in a subsequent stage of assembly with the receiver wherein, an upper portion of the retainer is captured by the receiver.

With reference to FIGS. 23-25, the retainer top surface 136 is moved into the receiver opening 91 as shown in FIG. 23 with the retainer top outer frusto-conical surface 150 shown in initial engagement with the receiver lower frusto-conical surface 110. The retainer upper portion 130 is then compressed as shown in FIG. 24, preferably with the aid of tooling (not shown) so that the retainer outer surfaces 150, 152 and 156 clear the receiver cylindrical surface 108 and inter into the receiver cavity 61 partially defined by the cylindrical surface 104 and the annular seating surface 106. Compression of the upper portion 130 occurs by pressing the upper portion radially inwardly causing a narrowing of the gaps or slots 144 and cooperating through bores 145 during pressing of the upper portion 130 in a radially inward direction toward the axis C. FIG. 24 shows the upper portion or collet 130 of the retainer 12 at a state of maximum compression. After the upper portion discontinuous surface 154 is moved upwardly into the receiver and travels past the receiver seating surface 106, the retainer 12 upper portion 130 is allowed to return to a neutral state that due the nature of the retainer material may not be the same as the original neutral state shown in FIG. 22, for example, prior to the compression step of FIG. 24. As shown in FIG. 25, the illustrated retainer surface 152 is still somewhat slanted inwardly and is not parallel to the receiver cylindrical surface 104 as might be expected and as might occur if the retainer 12 would have been made of a very resilient material. Even though the retainer upper portion 130 or collet is not in an original neutral position, the portion 130 has returned to a state wherein the upper collet portion annular ledge 154 is in contact with and captured by the receiver annular seating surface 106 from below and the receiver ceiling surface 103 from above to an extent that the retainer 12 upper portion 130 is now captured within the receiver cavity 61. It is foreseen that in other embodiments of the invention, the retainer upper portion may be introduced and fixed to the receiver in different ways, for example, the retainer and receiver may include helical threads and the retainer may be rotated into threaded engagement with the receiver.

Figure 26:
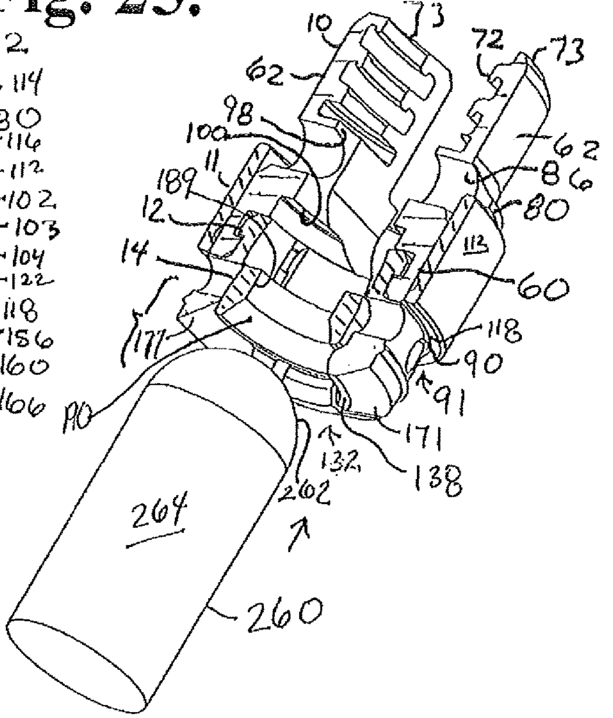
FIG. 26 is a reduced perspective view with portions broken away of the assembly as shown in FIG. 25 and further shown with a dilation driver tool shown in partial perspective view.
Figure 27:
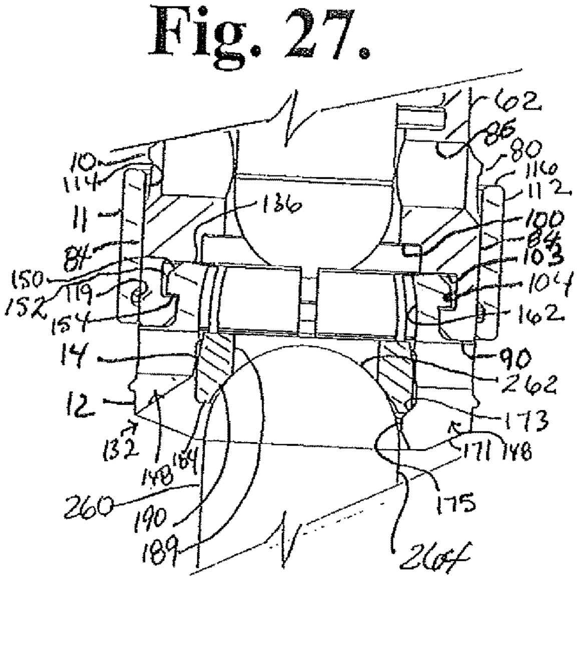
FIG. 27 is an enlarged front elevational view with portions broken away of the assembly and driver of FIG. 26 showing the driver in initial engagement with the retainer and the insert.
Figure 28:
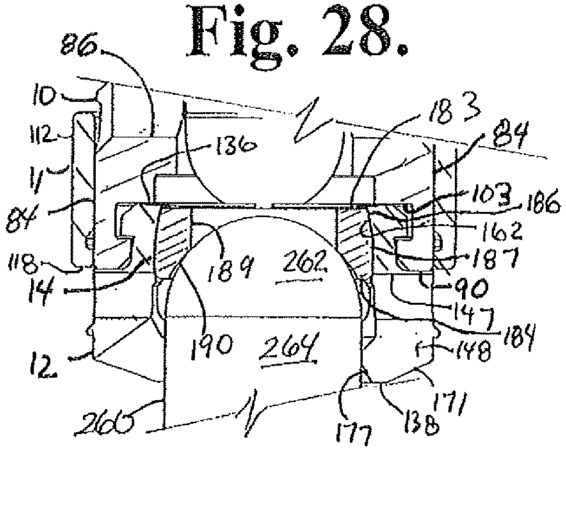
FIG. 28 is a front elevational view with portions broken away similar to FIG. 27 showing the driver pressing the insert upwardly into engagement with inner surfaces of the upper portion of the retainer.
Figure 29:
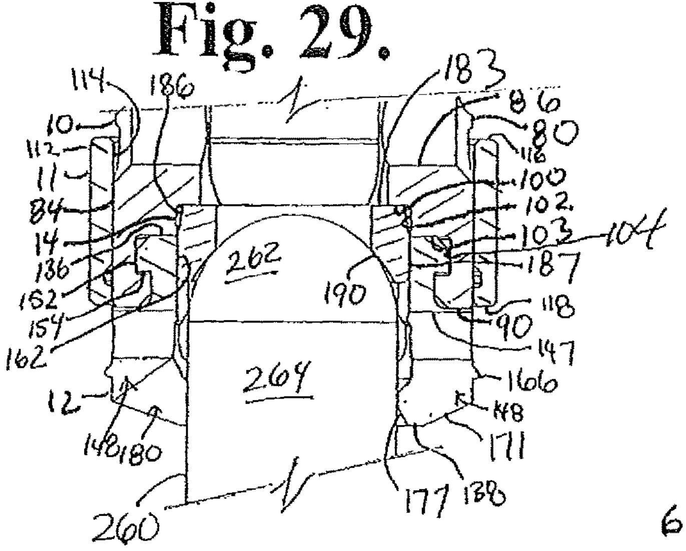
FIG. 29 is a front elevational view with portions broken away similar to FIG. 28 showing the driver subsequently further pressing the insert into abutment with a ceiling surface of the receiver, the insert dilating the retainer upper portion until outer surfaces thereof are pressed outwardly against a cylindrical surface of the receiver.

With reference to FIG. 26 a dilation tool is then used to position the insert 14 at a desirable location within the retainer 12 for a next step of assembly and also thereby press the retainer upper portion 130 outer surface 152 outwardly toward and against the receiver cylindrical surface 104. For this purpose, a dilation tool 260 of which only a portion is shown is used. The dilation tool includes a partially spherical driving surface 262 that transitions to a cylindrical holding surface 264. The tool 260 is sized and shaped to be slidably received into the retainer lower portion 132 at the surface 175 and the driving surface 262 has a radius that is the same or substantially similar to a radius of the compression insert surface 190. It is foreseen that the tool 260 may be part of a larger robotic apparatus that would include tooling for holding the receiver 10 at the opposed through bores 86 (and/or other locations along the receiver) and also, if needed, for holding the sleeve 11 out of the way of the retainer lower portion and in the desired location shown in FIG. 26. The tool 260 is inserted into the lower portion 132 of the retainer 12 with the forward surface 262 initially moving past the retainer surface 175 that defines a lower opening of the retainer 12 and into engagement with the lower spherical surface 190 of the compression insert 14. With reference to FIGS. 27 and 28, the tool 260 is moved upwardly in a direction toward the receiver arms 62 and pushes the insert 14 generally upwardly and thereby pushes the insert outer frusto-conical surface 186 into engagement with the resilient discontinuous surface 162 of the retainer upper portion 130, the insert 14 pressing the retainer upper portion 130 outwardly as the frusto-conical surface 186 moves upward and the larger diameter insert cylindrical surface 187 comes into engagement with the retainer inner surface 162 as shown in FIG. 28. With reference to FIG. 29, the tool 260 continues to press the insert 14 upwardly until the insert top surface 183 abuts against the receiver ceiling surface 100. At this time, the insert outer cylindrical surface 187 has pressed the retainer upper portion 130 outwardly to a maximum expanded position within the receiver 10 wherein the retainer outer cylindrical surface 152 is in engagement with the receiver inner cylindrical surface 104. The tool 260 is then pulled away from the insert lower surface 190 and removed from the retainer 12 lower portion 132.

Figure 30:
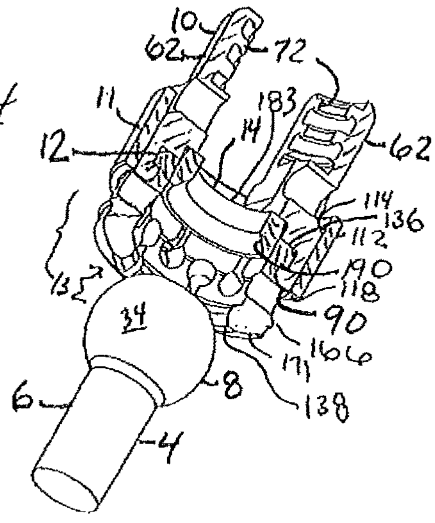
FIG. 30 is a reduced perspective view of the assembly of FIG. 29 after the dilation driver is removed and further showing the shank of FIG. 1 just prior to assembly with the retainer, the shank shown in partial perspective view.
Figure 35:
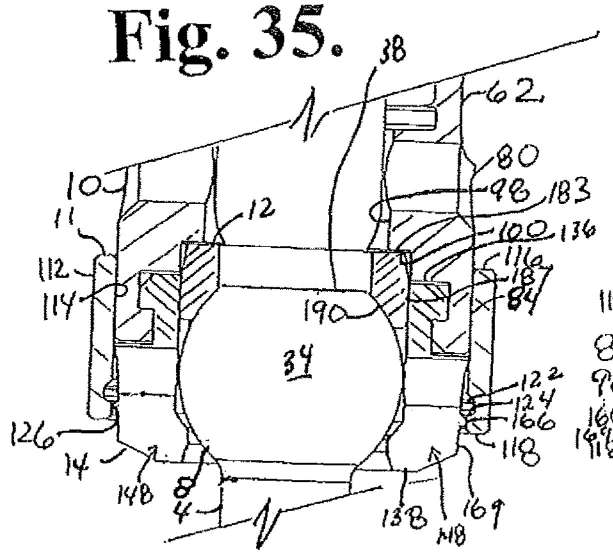
FIG. 35 is a front elevational view with portions broken away, similar to FIG. 34, showing the sleeve in a subsequent stage of assembly with the retainer, the sleeve pressing the lower portion of the retainer inwardly.
Figure 36:
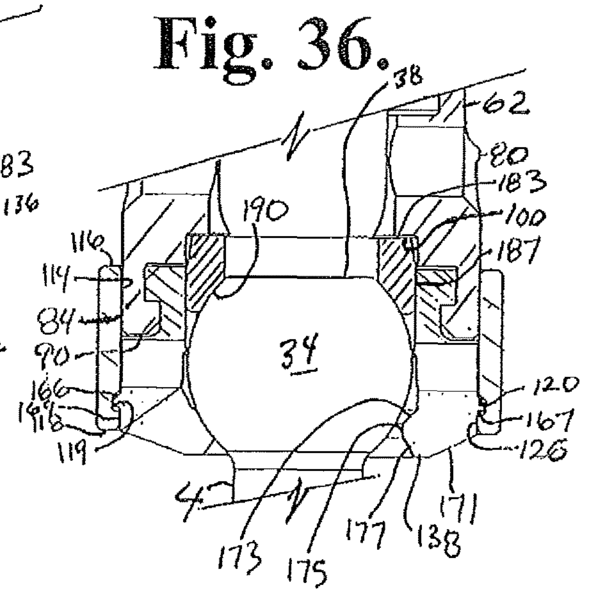
FIG. 36 is a front elevational view with portions broken away, similar to FIG. 35, showing an outer rim of the retainer being captured within a groove of the sleeve.
Figures 37, 38, 39, 40:
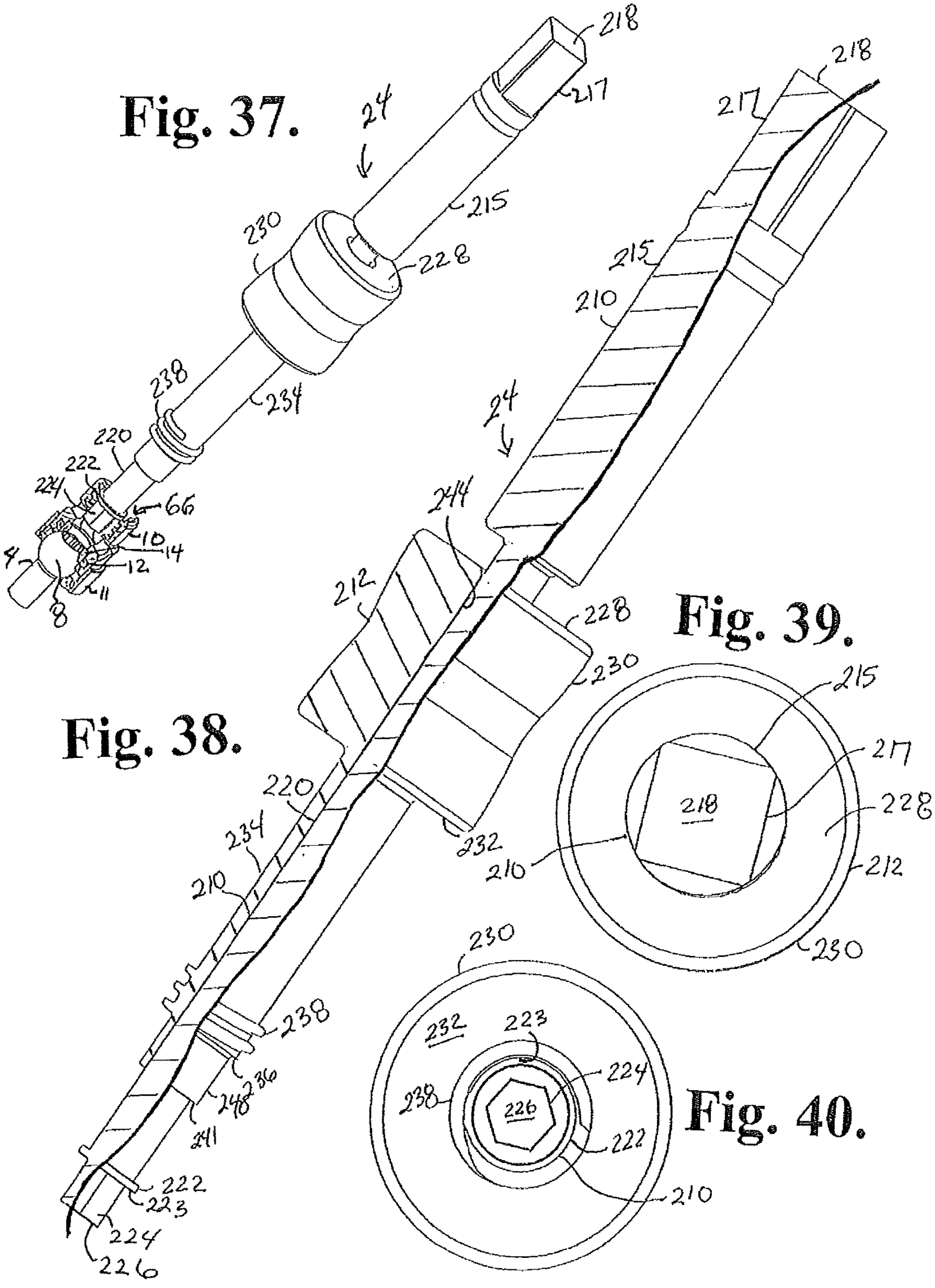
FIG. 37 is a reduced perspective view of the assembly of FIG. 36 further shown with a shank driver.
FIG. 38 is an enlarged front elevational view of the shank driver of FIG. 37 with portions broken away to show the detail thereof.
FIG. 39 is a top plan view of the driver of FIG. 38.
FIG. 40 is a bottom plan view of the driver of FIG. 38.

With reference to FIG. 30, at this time, the receiver, sleeve, insert and retainer combination is ready for assembly with the shank 4 at the factor or, alternatively, for shipping to an end user (e.g., surgical staff) who will thereafter assemble the combination with a desired shank 4. As shown in FIG. 39 the shank axis A and the receiver axis B are preferably aligned during assembly as shown in FIGS. 30-36. It is noted that although the retainer 12 upper portion is fixed to the receiver 10 with respect to axial or up and down movement along the receiver axis B, the retainer 12 may be rotated with respect to the receiver 10 about the receiver axis B. After assembly with the shank 4, but before insertion of a rod and closure top, the insert 14 may be placed into friction fit engagement with the shank head 8 as shown in FIGS. 37-43 and the receiver 10 may be placed at a desired angle with respect to the shank 4 as shown, for example, in FIGS. 44-46.

Figure 31:
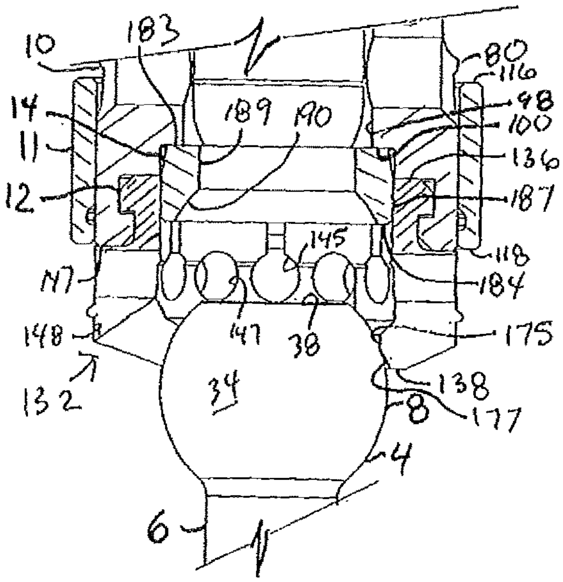
FIG. 31 is an enlarged front elevational view with portions broken away of the assembly of FIG. 30 showing the shank in an initial stage of assembly with the retainer.
Figure 32:
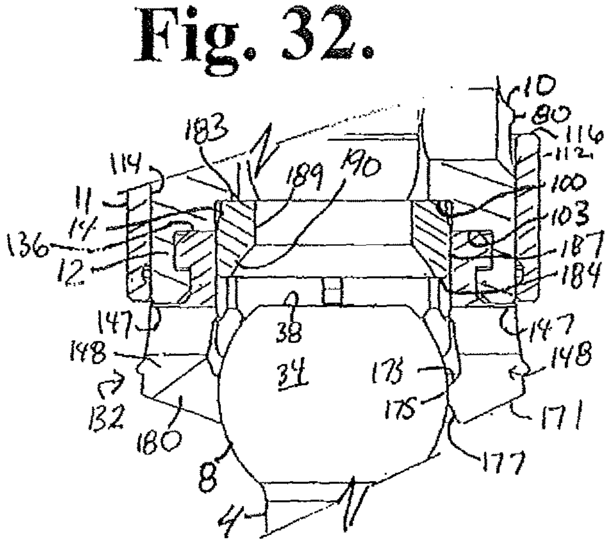
FIG. 32 is a front elevational view with portions broken away, similar to FIG. 31 showing a head of the shank in a subsequent stage of assembly with the retainer, pressing a lower portion of the retainer outwardly to a configuration of maximum expansion.
Figure 33:
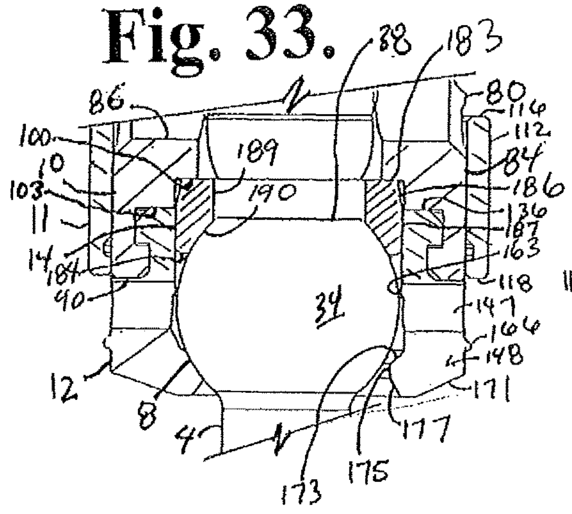
FIG. 33 is a front elevational view with portions broken away, similar to FIG. 32 showing the head of the shank pressed through the retainer lower portion and in engagement with the insert.
Figure 34:
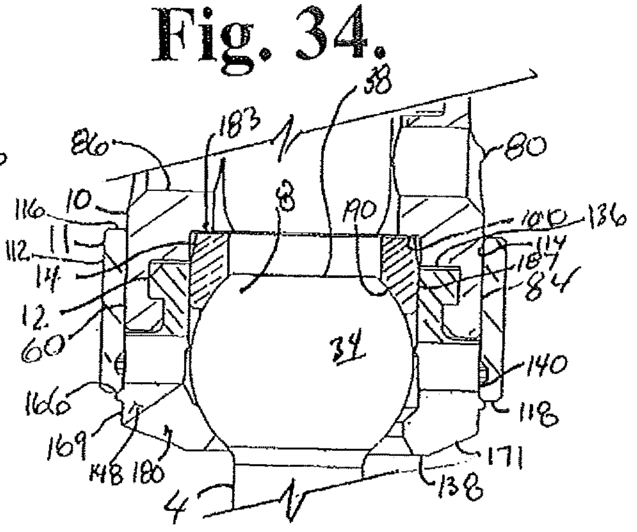
FIG. 34 is a front elevational view with portions broken away, similar to FIG. 33, showing the sleeve being lowered into a first stage of engagement with the retainer.

Returning to FIGS. 30-36, the shank 4 is assembled with the retainer 12 as follows: With reference to FIG. 30, the shank is positioned beneath the retainer lower portion 132 with the shank head 34 facing the retainer 12 outer lower surface 138 and the spherical surface 34 is then pressed against the retainer lower surface 177 as shown in FIG. 31. With reference to FIG. 32, the resilient retainer lower portion 132 is pressed radially outwardly at the surface 175 as the shank head 8 is moved upwardly toward the insert 14. With reference to FIG. 33, the shank head 8 is pressed upwardly into engagement with the insert spherical surface 190 and a hemisphere of the surface 34 passes through the most narrow opening of the retainer defined by the retainer discontinuous surface 175, the resilient lower portion 132 returning to a near neutral state capturing the shank head 8 therewithin. With reference to FIG. 34, the outer sleeve 11 is then moved downwardly toward the retainer outer lip 166, the sleeve inner surface 114 sliding along the retainer surface 140 and pressing the retainer lower outer surface 140 inwardly, thereby pressing the retainer lower portion 132 into an original neutral state and prohibiting subsequent expansion of the lower portion 132. With reference to FIGS. 35 and 36, the sleeve 11 is pressed further downwardly along the surface 149 until the retainer lip 166 is received in the sleeve inner groove defined by the sleeve surfaces 120, 122 and 124. With reference to FIG. 36, at this time, the sleeve 11 is fixed axially with respect to the retainer lower portion 132, the retainer lip 166 closely received by the sleeve sloping surface 120, inner cylindrical surface 122 and bottom seat 124. Any upward force placed on the sleeve 11 causes the lip lower ledge 167 to abut against the sleeve groove bottom seat 124. The sleeve lower inner cylindrical surface 126 is now fixed axially into position facing the retainer lower cylindrical surface 169. It is noted that such axial fixing of the sleeve 11 with respect to the retainer 12 does not prohibit the retainer 12 from rotating with respect to the receiver 10 about the receiver axis B.

Figure 41:
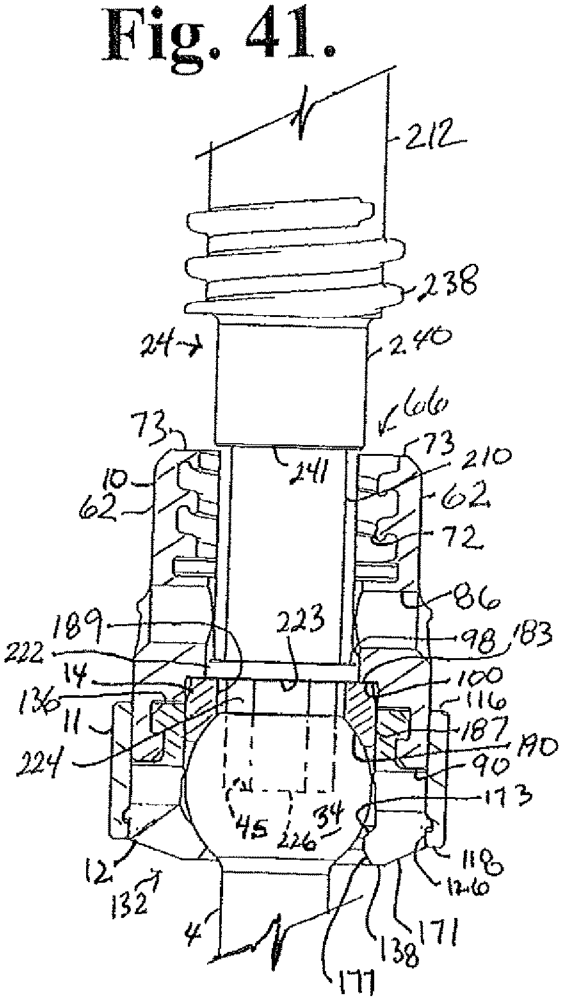
FIG. 41 is an enlarged front elevational view with portions broken away of the assembly and driver of FIG. 37, the driver end being shown inserted into a drive aperture of the shank upper portion or head.
Figure 42:
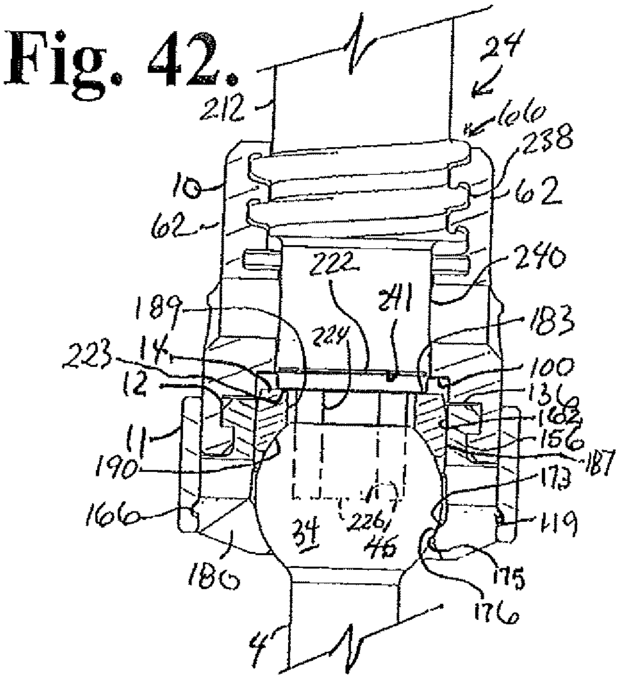
FIG. 42 is a front elevational view with portions broken away, similar to FIG. 41, the driver being shown pressing the insert downwardly into a friction fit engagement with the shank head that in turn presses the shank downwardly into engagement with the retainer lower portion.
Figure 43:
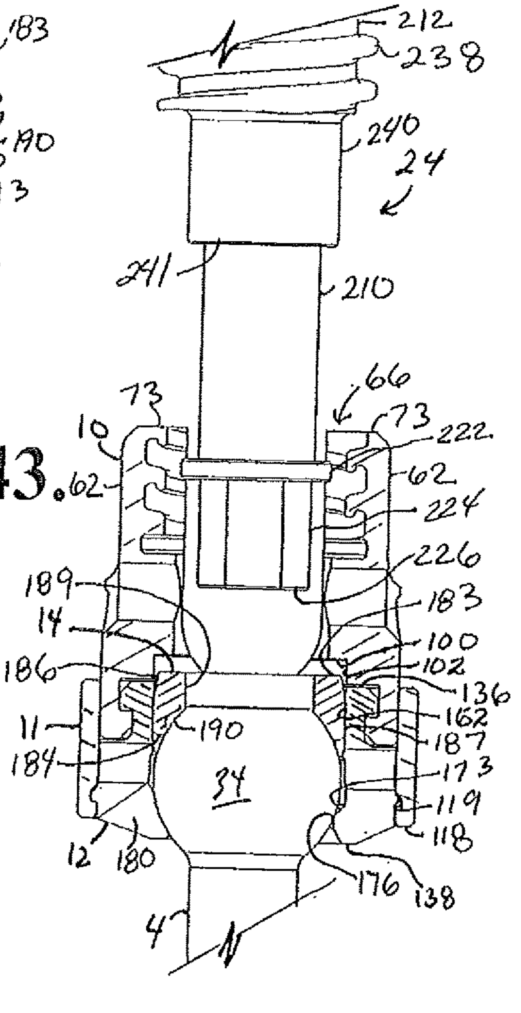
FIG. 43 is a front elevational view with portions broken away, similar to FIG. 42, the driver being shown being removed from the shank head and out of the receiver, leaving the shank head in non-floppy but movable friction fit engagement with both the insert and the retainer.

With reference to FIGS. 37-43, the driving tool 24 may then be used to push the insert 14 down toward the receiver base or bottom 90 to an extent that an engagement between the insert surface 190 and the shank spherical surface 34 is a non-locking friction fit. Such friction fit engagement allows for non-floppy pivoting movement of the shank 4 with respect to the retainer 12 (and thus with respect to the receiver 10) with some force and such temporary desired angular orientation will hold in place during surgery until ultimately frictionally locked in place near an end of the surgical procedure. Thus, with reference to FIG. 37, the driver 24 is inserted into the receiver upper opening 66 with the tool hex driver 224 directed toward the shank internal drive 46. With reference to FIG. 41, the hex driver 224 is inserted until the driver tip 226 engages the shank internal drive base surface 45. With reference to FIG. 42, the driver outer holder 212 is then slid downwardly along the inner drive cylindrical surface 220 until the guide and advancement structure 238 comes into engagement with the receiver guide and advancement structure 72. The outer holder 212 is then rotated so that the guide and advancement structure 238 helically mates with the guide and advancement structure 72 of the receiver 10. As the outer tool 212 is rotated, the outer tool end surface 241 abuts against the driver lip 222 pressing the driver lip bottom surface 223 downwardly against the insert 14 top surface 183 and also pressing the driver tip 226 downwardly against the shank drive seat 45 thus pressing the shank head 8 downwardly against the inner upper edge 176 of the surface 175 of the retainer lower portion 132. As shown in FIG. 43, when the outer drive tool is rotated in reverse to unscrew the guide and advancement structure 238 from the receiver flange form 72 and the driver 225 is removed from the shank internal drive 46, the insert 14 is retained in a friction fit engagement with the shank head surface 34 because the insert outer surface 187 is in a fixed frictional engagement with the retainer upper portion discontinuous inner surface 162.

Figure 44:
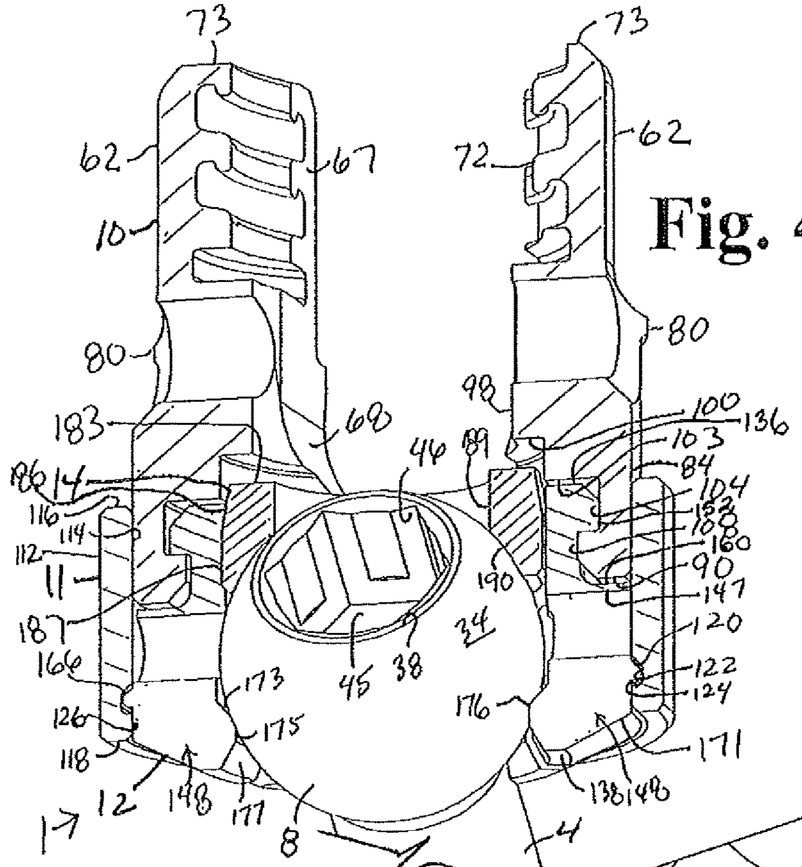
FIG. 44 is an enlarged front elevational view with portions broken away of the assembly of FIG. 43, showing the retainer rotated and the shank pivoted at an angle with respect to the retainer and insert with the use of some force.
Figure 46:
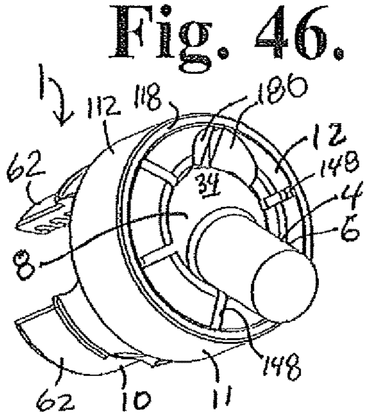
FIG. 46 is a reduced perspective view of the assembly of FIG. 45 with the shank being pivoted to a different position (thirty degree shank angulation with respect to the receiver).
Figure 45:
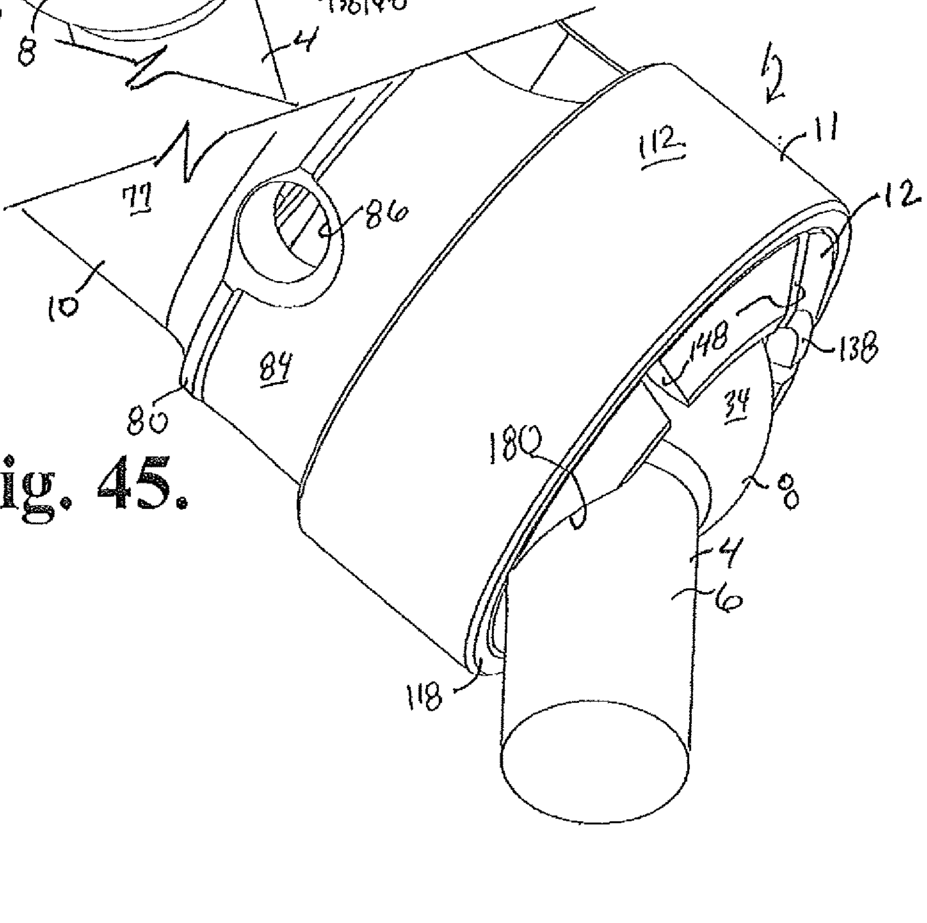
FIG. 45 is an enlarged and partial perspective view of the assembly of FIG. 44 illustrating a fifty-four degree angulation of the shank with respect to the receiver.

With reference to FIGS. 44-46, at this time, the receiver 10 may be articulated to a desired angular position with respect to the shank 4 prior to insertion of the rod 21 or closure top 18, that will be held, but not locked, by frictional engagement between the insert 14 (that is now locked against the retainer 12) and the shank head spherical surface 34. FIG. 44 illustrates a fifty-four degree sagittal plane angulation of the shank 4 with respect to the receiver 10 with the shank body 6 received in the retainer cut-out 180. FIG. 44 illustrates another fifty-four degree angulation of the shank 4 with respect to the receiver 10, but wherein the retainer 12 has been rotated with respect to the receiver 10 about the receiver axis B to an arbitrary location desired by a surgeon that will hold in such non-locked but also non-floppy position by the friction fit engagement between the insert 14 and the shank head 8 until moved by force to another orientation. FIG. 46 illustrates an alternative thirty degree angular position of the shank 4 with respect to the receiver 10 showing the shank body 6 pivoted away from the retainer cut-out 180.

The assembly 1 made up of the assembled shank 4, receiver 10, sleeve 11, retainer 12 and compression insert 14, is screwed into a bone, such as the vertebra 17, by rotation of the shank 4 using a suitable driving tool, such as the tool 24, for example, that operably drives and rotates the shank body 6 by engagement thereof at the internal drive 46. In other embodiments of the assembly 1 of the invention, for example, for use with the thoracic or lumbar spine wherein the bone screw shank 4 is relatively larger, the shank 4 may be cannulated. In some procedures, the vertebra 17 may be pre-drilled to minimize stressing the bone and have a guide wire (not shown) inserted therein to provide a guide for the placement and angle of the shank 4 (in embodiments wherein the shank is cannulated) with respect to the vertebra. A further tap hole may be made using a tap with the guide wire as a guide. Then, the assembly 1 may be threaded onto the guide wire utilizing the cannulation bore. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires. In other larger embodiments, the shank 4 may be driven into the vertebra 17 without the remainder of the assembly 1 and the assembly 1 is then pressed onto the shank head 8. In such embodiments, the shank 4 may either be driven to a desired final location or may be driven to a location slightly above or proud to provide for ease in assembly with the pre-assembled receiver, compression insert and retainer.

Figure 49:
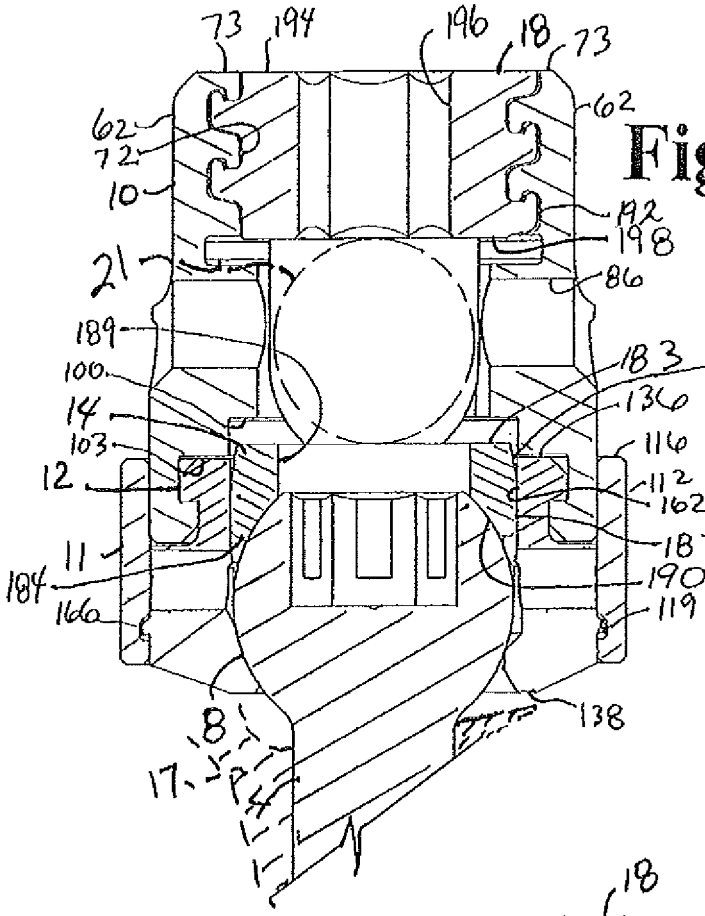
FIG. 49 is an enlarged front elevational view of the assembly of FIG. 47 wherein the shank was pivoted into a nominal or coaxial relation with the receiver prior to assembly with the rod and closure top, and with portions broken away to show the detail thereof.
Figure 50:
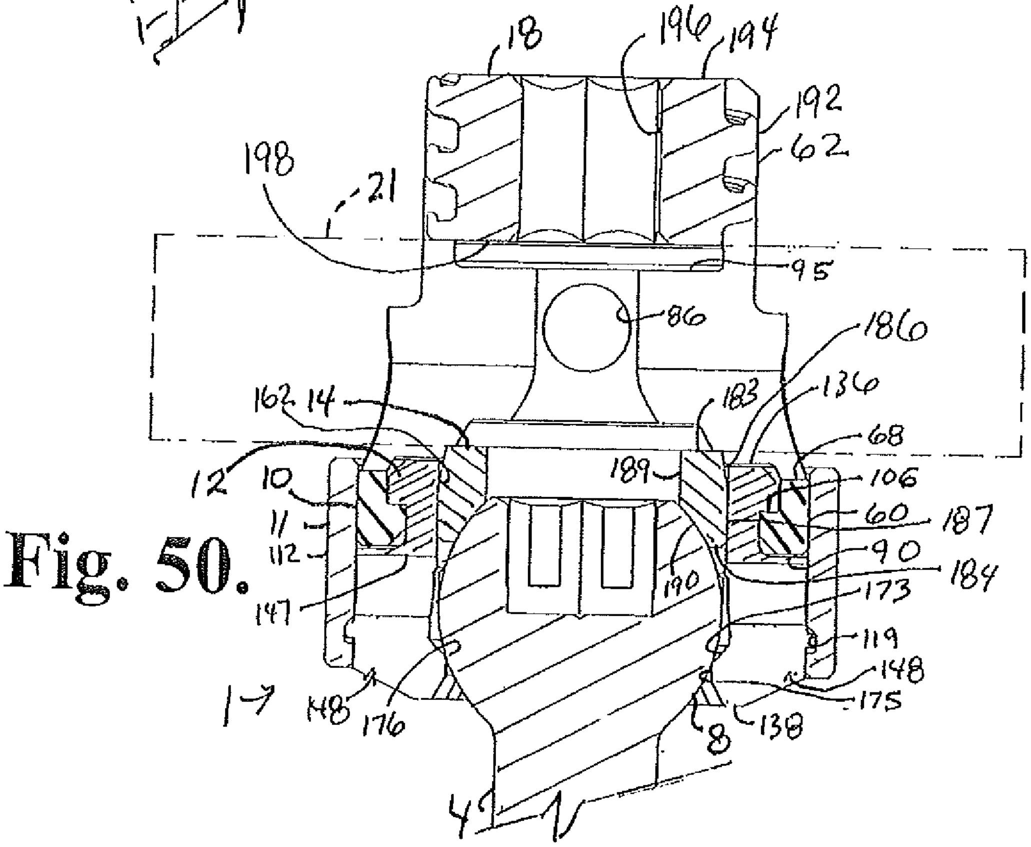
FIG. 50 is a side elevational view of the assembly of FIG. 49 with portions broken away to show the detail thereof.

With reference to FIGS. 47-50, in the illustrated embodiment, the rod 21 is eventually positioned in an open or percutaneous manner in cooperation with the at least two bone screw assemblies 1. The closure structure 18 is then inserted into and advanced between the arms 62 of each of the receivers 10. The closure structure 18 is rotated, using a tool engaged with the inner drive 196 until a selected pressure is reached at which point the rod 21 engages the top surface 183 of the compression insert 14, pressing the insert surface 190 into locked frictional engagement with the shank spherical surface 34. The insert 14 also urges the shank upper portion 8 toward the retainer edge surface 176 and into locking engagement therewith, the retainer 12 frictionally abutting and expanding outwardly against the sleeve 11. FIGS. 47 and 48 show the assembly one in such a locked position wherein the shank 4 had been previously pivoted with respect to the receiver to a fifty-four degree angle with the shank body 6 received in the retainer cut-out 180. FIGS. 49 and 50 show the assembly 1 in a locked position with the shank 4 axially aligned with the receiver axis B.

It is to be understood that while certain forms of the present invention have been illustrated and described herein, it is not to be limited to the specific forms or arrangement of parts described and shown.

What is claimed is:

1. A receiver assembly intended for securing an elongate rod to a head of a shank via tooling and a closure top, the shank having an anchor portion opposite the head configured for attachment to a bone of a patient, the receiver assembly comprising:

a lower collet retainer portion of a receiver comprising an inner surface defining a center through aperture communicating with a bottom of the lower collet retainer portion through a lower collet opening, the inner surface configured to resiliently expand to receive the head of the shank into the center through aperture upon the head being uploaded through the lower collet opening;

a housing portion of the receiver above the lower collet retainer portion, the housing portion comprising a pair of upright arms extending above the lower collet retainer portion to define an open channel configured to receive the elongate rod, and an upper portion of a central bore configured to receive the closure top entirely therein, the central bore extending downward from top surfaces of the upright arms, through the open channel and through the lower collet retainer portion; and an outer sleeve member movable relative to the lower collet retainer portion with the tooling between a first position defining a first expandable configuration of the lower collet retainer portion and a second position defining a second non-expandable and lockable configuration of the lower collet retainer portion, a load ring being positionable within the center through aperture of the lower collet retainer portion prior to the head of the shank, wherein the load ring further comprises a lower outer cylindrical surface extending downward toward a bottom surface of the load ring and an upper outer frustoconical surface extending upward toward a top surface of the load ring, wherein the outer sleeve member is configured for movement by the tooling from the first position to the second position so as to secure the head of the shank in the lower collet retainer portion after the head of the shank has been uploaded into the center through aperture of the lower collet retainer portion and received therein.

2. The receiver assembly of claim 1, wherein the lower collet retainer portion is formed separate from the housing portion and attached thereto via at least a portion of the lower collet retainer portion being uploaded into an internal surface of a lower end of the housing portion.

3. The receiver assembly of claim 1, further comprising a plurality of slots extending upwardly from the lower collet opening and at least partially through the inner surface of the lower collet retainer portion to provide for resilient expansion of the lower collet retainer portion.

4. The receiver assembly of claim 1, wherein the load ring further comprises a spherical contact surface configured to engage a spherical outer surface of the head of the shank with a friction fit engagement.

5. A pivotal bone anchor assembly comprising the receiver assembly of claim 4 and further comprising the shank and the closure top, wherein prior to locking the position of the shank in the lower collet retainer portion of the receiver by force from the closure top, the load ring is configured to be moved downward within the central bore of the housing portion to establish the friction fit engagement between the spherical contact surface of the load ring and the spherical outer surface of the head of the shank.

6. The pivotal bone anchor assembly of claim 5, wherein the closure top is configured for positioning entirely within the upper portion of the central bore of the housing portion above the elongate rod and in engagement with a mating structure formed into inner surfaces of the upright arms to apply a downward pressure to a top of the elongate rod, so as to secure the elongate rod to the bone of the patient.

7. A pivotal bone anchor assembly intended for securing an elongate rod to a bone of a patient, the pivotal bone anchor assembly comprising:

a shank comprising a head having a spherical outer surface and an anchor portion opposite the head configured for attachment to the bone;

a lower retaining portion of a receiver having an inner surface defining a center through aperture configured to receive the head of the shank and communicating with a bottom of the lower retaining portion through a lower opening;

a housing portion of the receiver above the lower retaining portion, the housing portion comprising:

a central bore centered about a vertical centerline axis;

an upper housing portion including a pair of upright arms defining an open channel configured to receive the elongate rod and an upper portion of the central bore communicating with the open channel and configured to receive a closure top; and a lower housing portion including an internal surface configured to receive at least a portion of the lower retaining portion in a first expandable configuration in which the inner surface of the lower retaining portion is configured to expandingly receive the head of the shank upon the head of the shank being uploaded into the center through aperture through the lower opening; and a load ring configured for positioning into the center through aperture of the lower retaining portion prior to uploading the head of the shank, the load ring having a center opening configured to receive a drive tool therethrough, a top surface configured for engagement by the elongate rod, and a lower concave surface configured to engage the head of the shank, wherein the load ring further comprises a lower outer cylindrical surface extending downward toward an annular bottom surface of the load ring and an upper outer frustoconical surface extending upward toward the top surface, wherein after the head of the shank has been uploaded into the center through aperture of the lower retaining portion and secured in the lower retaining portion, the load ring is configured for downward compression against the head of the shank by force from the closure top applied to the elongate rod so as to lock a position of the shank in the lower retaining portion.

8. The pivotal bone anchor assembly of claim 7, wherein the lower concave surface of the load ring further comprises a spherical contact surface configured to engage the spherical outer surface of the head of the shank with a non-floppy friction fit engagement.

9. The pivotal bone anchor assembly of claim 8, wherein prior to locking the position of the shank in the lower retaining portion by force from the closure top, the load ring is configured to be moved downward within the central bore of the housing portion to establish the non-floppy friction fit engagement between the lower concave surface of the load ring and the spherical outer surface of the head of the shank.

10. The pivotal bone anchor assembly of claim 7, wherein the lower retaining portion is formed separate from the housing portion and attached thereto upon being uploaded into the internal surface of the lower housing.

11. The pivotal bone anchor assembly of claim 7, wherein the lower retaining portion further comprises a plurality of slots extending upwardly from the lower opening.

12. The pivotal bone anchor assembly of claim 7 and further comprising an outer sleeve configured for positioning on the housing portion of the receiver at least partially above the lower retaining portion when the lower retaining portion is positioned in the first expandable configuration, wherein after the head of the shank is uploaded into the lower retaining portion, the outer sleeve is configured for downward slidable translation relative to the housing portion into an engagement with an outer surface of the lower retaining portion that defines a second non-expandable configuration of the lower retaining portion in which the head of the shank is secured in the lower retaining portion.

13. The pivotal bone anchor assembly of claim 12, wherein a top surface of the outer sleeve is spaced below the elongate rod when the pivotal bone anchor assembly is in a locked configuration.

14. The pivotal bone anchor assembly of claim 12, wherein the top surface of the load ring is a flat annular surface located above a top surface of the outer sleeve when the pivotal bone anchor assembly is in a locked configuration.

15. The pivotal bone anchor assembly of claim 12, wherein the closure top is configured for positioning entirely within the central bore of the upper housing portion above the elongate rod and in engagement with a mating structure formed into inner surfaces of the upright arms to apply a downward pressure to a top of the elongate rod, so as to secure the elongate rod to the bone of the patient.

16. A pivotal bone anchor assembly intended for securing an elongate rod to a bone of a patient, the pivotal bone anchor assembly comprising:

a shank comprising a head having a spherical outer surface and an anchor portion opposite the head configured for attachment to the bone;

a lower retaining portion of a receiver having an inner surface defining a center through aperture configured to receive the head of the shank and communicating with a bottom of the lower retaining portion through a lower opening;

a housing portion of the receiver above the lower retaining portion, the housing portion comprising:

a central bore centered about a vertical centerline axis;

an upper housing portion including a pair of upright arms defining an open channel configured to receive the elongate rod and an upper portion of the central bore communicating with the open channel and configured to receive a closure top; and a lower housing portion including an internal surface configured to receive at least a portion of the lower retaining portion uploaded into the upper housing portion in which the inner surface of the lower retaining portion is configured to receive the head of the shank upon the head of the shank being uploaded into the lower retaining portion through the lower opening; and a load ring configured for positioning within the assembly prior to uploading the head of the shank, the load ring having a center opening configured to receive a drive tool therethrough, a top surface configured for engagement by the elongate rod, and a lower concave surface configured to engage the head of the shank, wherein the load ring further comprises a lower outer cylindrical surface extending downward toward an annular bottom surface of the load ring and an upper outer frustoconical surface extending upward toward the top surface, wherein after the head of the shank has been uploaded into the center through aperture of the lower retaining portion and secured in the lower retaining portion, the load ring is configured for downward compression against the head of the shank by force from the closure top applied to the elongate rod so as to lock a position of the shank in the lower retaining portion.

17. The pivotal bone anchor assembly of claim 16, wherein the lower concave surface of the load ring further comprises a spherical contact surface configured to engage the spherical outer surface of the head of the shank with a non-floppy friction fit engagement.

18. The pivotal bone anchor assembly of claim 17, wherein prior to locking the position of the shank in the lower retaining portion by force from the closure top, the load ring is configured to be moved downward within the central bore of the housing portion to establish the non-floppy friction fit engagement between the lower concave surface of the load ring and the spherical outer surface of the head of the shank.

19. The pivotal bone anchor assembly of claim 16 and further comprising an outer sleeve configured for positioning on the housing portion of the receiver at least partially above the lower retaining portion when the lower retaining portion is positioned in a first expandable configuration, wherein after the head of the shank is uploaded into the lower retaining portion, the outer sleeve is configured for downward slidable translation relative to the housing portion into an engagement with an outer surface of the lower retaining portion that defines a second non-expandable and lockable configuration of the lower retaining portion in which the head of the shank is secured in the lower retaining portion.

20. The pivotal bone anchor assembly of claim 19, wherein a top surface of the outer sleeve is spaced below the elongate rod when the pivotal bone anchor assembly is in a locked configuration.

21. The pivotal bone anchor assembly of claim 19, wherein the top surface of the load ring is a flat annular surface located above a top surface of the outer sleeve when the pivotal bone anchor assembly is in a locked configuration.

* * * * *